(12) United States Patent
Zeng et al.

(10) Patent No.: US 11,744,957 B2
(45) Date of Patent: Sep. 5, 2023

(54) PEN NEEDLE ASSEMBLY APPARATUS

(71) Applicant: Embecta Corp., Andover, MA (US)

(72) Inventors: Xi Zeng, Suzhou (CN); Huasheng Huang, Suzhou (CN); Wei Hu, Shanghai (CN); Junyu Zhou, Shanghai (CN)

(73) Assignee: Embecta Corp., Andover, MA (US)

( * ) Notice: Subject to any disclaimer, the term of this patent is extended or adjusted under 35 U.S.C. 154(b) by 555 days.

(21) Appl. No.: 16/957,689

(22) PCT Filed: Dec. 19, 2018

(86) PCT No.: PCT/US2018/066539
§ 371 (c)(1),
(2) Date: Jun. 24, 2020

(87) PCT Pub. No.: WO2019/133392
PCT Pub. Date: Jul. 4, 2019

(65) Prior Publication Data
US 2020/0360622 A1    Nov. 19, 2020

(30) Foreign Application Priority Data

Dec. 28, 2017   (CN) ......................... 2017/11456114.7
Dec. 28, 2017   (CN) ......................... 2017/21886196.4

(51) Int. Cl.
*A61M 5/32*     (2006.01)
*A61M 5/34*     (2006.01)

(52) U.S. Cl.
CPC ........ *A61M 5/3213* (2013.01); *A61M 5/3205* (2013.01); *A61M 5/34* (2013.01); *A61M 5/3202* (2013.01)

(58) Field of Classification Search
CPC .............. A61M 5/3202; A61M 5/3204; A61M 5/3205; A61M 5/321; A61M 5/3213
See application file for complete search history.

(56) References Cited

U.S. PATENT DOCUMENTS 4,375,849 A * 3/1983 Hanifl ................. A61M 5/3205
                                                                206/63.5
4,738,362 A * 4/1988 Burns ................. A61M 5/3205
                                                                206/63.5
(Continued)

FOREIGN PATENT DOCUMENTS

AU    2009202158 A1    12/2009
EP    1 321 157 A2    6/2003
(Continued)

OTHER PUBLICATIONS

JP-2009225825-A Translation From Espacenet (Year: 2009).*
(Continued)

*Primary Examiner* — Michael W Hotchkiss
(74) *Attorney, Agent, or Firm* — Greenberg Traurig, LLP; Roman Fayerberg; David J. Dykeman

(57) ABSTRACT

A pen needle assembly apparatus includes a housing (30), a movable gripping assembly (32) for gripping a pen needle assembly (18), and an actuator (108). The housing (30) has a top end (34), a bottom end (36), and an inner cavity (38) for storing used pen needle assemblies. The gripping assembly (32) in one embodiment includes two movable jaws (58) that are movable to engage and grip the outer cover (22) of the pen needle assembly (18) so that the needle hub (16) can be separated from the outer cover (22) and placed back in the outer cover (22) after use of the pen needle. The actuator (108) is connected to the jaws (58) where movement of the actuator separates the jaws to release the outer cover of the pen needle assembly. The housing (30) has an opening 160) for engaging the inner shield (24) of the pen needle assembly to remove the inner shield (24) from the needle hub (16).

20 Claims, 19 Drawing Sheets

(56) References Cited

U.S. PATENT DOCUMENTS

| | | | | |
|---|---|---|---|---|
| 4,801,013 | A | * | 1/1989 | Bruno ................ A61M 5/3205 206/366 |
| 4,986,811 | A | * | 1/1991 | Thead ................ A61M 5/3205 604/110 |
| 4,989,307 | A | * | 2/1991 | Sharpe ................ A61M 5/3205 128/917 |
| 4,995,871 | A | * | 2/1991 | Sasaki ................ A61M 5/3205 220/348 |
| 5,024,666 | A | * | 6/1991 | Pituch ................ A61M 5/3213 604/263 |
| 5,086,922 | A | * | 2/1992 | Sagstetter ........... A61M 5/3205 604/198 |
| 5,187,850 | A | * | 2/1993 | McCammon ....... A61M 5/3205 29/235 |
| 5,273,161 | A | * | 12/1993 | Sagstetter ........ A61B 5/150389 220/908 |
| 5,275,280 | A | * | 1/1994 | Everhart ............. A61M 5/3205 206/370 |
| 5,312,346 | A | * | 5/1994 | Han .................... A61M 5/3205 604/110 |
| 5,469,964 | A | * | 11/1995 | Bailey ................ A61M 5/3213 206/370 |
| 5,947,950 | A | * | 9/1999 | Shillington ......... A61M 5/3205 206/370 |
| 6,247,592 | B1 | * | 6/2001 | Racicot ............... A61M 5/3205 220/908 |
| D482,448 | S | * | 11/2003 | Crawford ..................... D24/131 |
| 8,875,882 | B1 | * | 11/2014 | Salloum .............. A61M 5/3205 206/366 |
| 8,876,780 | B2 | * | 11/2014 | Bruehwiler ........... A61M 5/343 604/176 |
| 9,283,328 | B2 | * | 3/2016 | Dasbach ............ A61M 5/3276 |
| 9,579,469 | B2 | * | 2/2017 | Limaye .............. A61M 5/3278 |
| 9,694,143 | B2 | * | 7/2017 | Dasbach ............. A61M 5/347 |
| 10,258,746 | B2 | * | 4/2019 | Radmand ........... A61M 5/3276 |
| 10,471,221 | B2 | * | 11/2019 | Tsukamoto ........... A61M 5/347 |
| 2005/0056121 | A1 | * | 3/2005 | Lyman ..................... B67B 7/00 81/3.07 |
| 2005/0236289 | A1 | * | 10/2005 | Tanaka ................ A61M 5/3205 206/370 |
| 2005/0269226 | A1 | * | 12/2005 | Erickson ............ A61M 5/3205 206/363 |
| 2005/0288636 | A1 | * | 12/2005 | Gerald Cooley ... A61M 5/3205 604/27 |
| 2009/0014462 | A1 | * | 1/2009 | Costa .................. A61M 5/3205 221/185 |
| 2012/0145577 | A1 | * | 6/2012 | Bode ................... A61M 5/3276 414/431 |
| 2013/0150804 | A1 | * | 6/2013 | Bianco ................ A61M 5/3205 604/241 |
| 2014/0082933 | A1 | * | 3/2014 | Jugl .................... A61M 5/3205 29/700 |
| 2015/0297837 | A1 | * | 10/2015 | Schraga .................. A61M 5/34 604/239 |
| 2017/0209230 | A1 | * | 7/2017 | Nakagami ........... A61B 50/362 |
| 2022/0401656 | A1 | * | 12/2022 | Pryor ................ A61M 5/31568 |

FOREIGN PATENT DOCUMENTS

| | | | |
|---|---|---|---|
| EP | 1321157 | A2 | 6/2003 |
| EP | 1 598 043 | A1 | 11/2005 |
| EP | 1 614 439 | A1 | 1/2006 |
| JP | 2009225825 | A * | 10/2009 .......... A61M 5/3205 |
| WO | 2009136193 | A1 | 11/2009 |
| WO | 2010/124974 | A2 | 11/2010 |
| WO | WO-2013146868 | A1 * | 10/2013 ............. A61G 12/00 |

OTHER PUBLICATIONS

WO-2013146868-A1 Translation From Espacenet (Year: 2013).*
International Search Report dated Mar. 22, 2019, which issued in the corresponding PCT Patent Application PCT/US2018/066539.

* cited by examiner

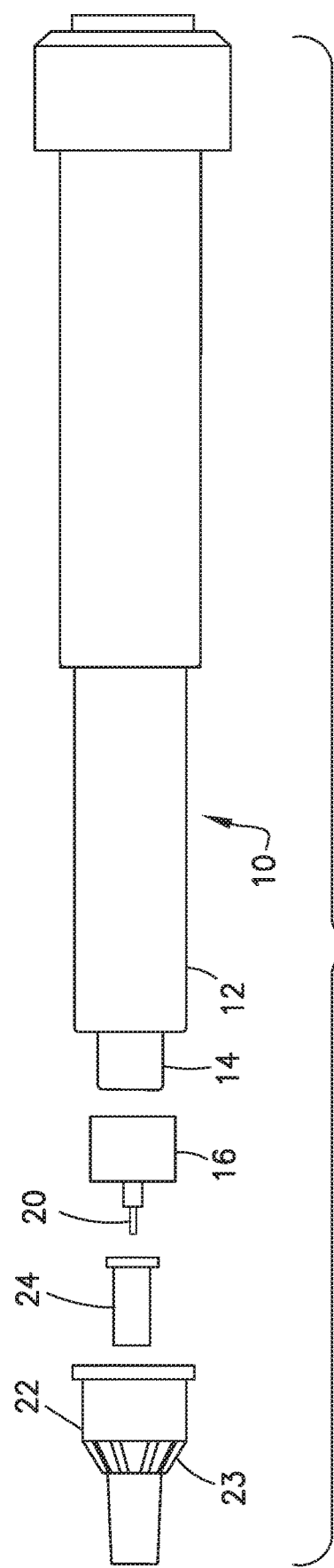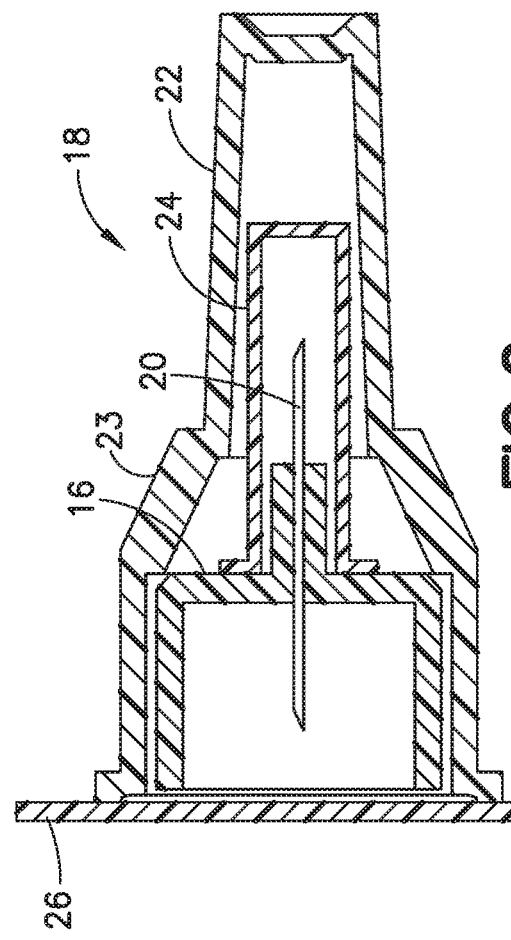

PEN NEEDLE ASSEMBLY APPARATUS

This application claims priority to Chinese Application No. 2017/21886196.4 filed Dec. 28, 2017 and Chinese Application No. 2017/11456114.7 filed Dec. 28, 2017, which are hereby incorporated by reference in their entirety.

FIELD OF THE INVENTION

The present invention relates generally to an apparatus for use in mounting and attaching a pen needle assembly to a delivery device, such as a pen delivery device. The apparatus has a well or opening for retaining a needle hub having an inner shield covering a cannula on the needle hub and to retain the needle hub after use to reduce the risk of inadvertent needle stick. The apparatus has a second well to receive the inner shield for separating the inner shield from the needle hub without the need to handle the inner shield.

BACKGROUND OF THE INVENTION

Insulin and other injectable medications are commonly delivered with drug delivery pens, whereby a disposable pen needle hub is attached to the pen to facilitate drug container access and allow fluid egress from the container through the needle into the patient.

Various pen needle delivery devices are known in the art for dispensing the substance to the patient. The delivery devices often use a disposable needle hub having a cannula or needle extending from a patient end of the hub for inserting into the patient. A non-patient end of the hub is coupled to the pen delivery device for delivering the substance to the patient.

The needle hub assembly is often packaged in a container containing several loose needle hubs. A needle hub is selected from the package and attached to the pen needle delivery device for injecting the patient and then removed to be discarded. The needle hub package includes an outer cover that encloses the needle hub and a removable seal that is peeled from the outer cover to open the cavity so that the needle hub can be removed. The needle hub can have threaded non-patient end that is threaded onto the delivery device. The delivery device with the attached needle hub is then removed from the outer cover. An inner needle shield is attached to the needle hub to cover the cannula until the device is ready for use. The shield is removed to expose the cannula for use to deliver the substance to the patient. After use, the needle hub can be inserted back into the outer cover to enclose the exposed cannula. The pen delivery device is separated from the needle hub leaving the needle hub within the outer cover.

The prior devices require the use of both hands to connect to and remove the needle hub from the delivery device. During the placement back into the outer cover, the cannula is exposed and provides an increased risk of accidental needle stick. The manual operation of holding the outer cover while positioning the spent needle hub and cannula into the cavity of the outer cover can be difficult without accidental needle stick.

Existing pen needle assemblies are disclosed in U.S. Patent Application Publication Nos. 2006/0229562 to Marsh et al. and 2007/0149924 to R. Marsh, the entire contents of both of which are hereby incorporated by reference.

Although the prior devices have been suitable for the intended use, there is a continuing need in the industry for improved packaging for a pen needle hub assembly.

SUMMARY OF THE INVENTION

The present invention is directed to an apparatus and device for receiving and supporting at least one pen needle assembly for attaching the pen needle assembly to a delivery device, such as a delivery pen. In particular, the invention is directed to an apparatus for a pen needle assembly that can be used in a manner to reduce the risk of inadvertent needle stick while attaching and removing the pen needle assembly from the delivery pen.

The apparatus includes a housing, and movable gripping assembly, and an actuator to operate the gripping assembly. In one embodiment, the apparatus is provided with an opening or well for a pen needle assembly. The pen needle assembly includes an outer cover, a needle hub supporting a cannula or needle, and an inner shield covering the cannula. A removable seal closes the open end of the outer cover that is removed before attaching the needle hub to the delivery pen. The apparatus retains and supports the pen needle assembly and the needle hub and cannula while attaching to a delivery pen or other delivery device. The apparatus is able to store a used needle hub and the outer cover for disposal. The apparatus has a recess or well for receiving and retaining the inner shield that covers the cannula so that the inner shield can be removed from the needle hub without the operator handling the inner shield. The used needle hub can be inserted back into the outer cover and transferred to a storage tray or internal sharps container for disposal. The inner shield can be re-attached to the needle hub or discarded in the storage tray. The actuator is provided to operate the gripping assembly and release the needle hub, outer cover, and inner shield to a suitable disposal bin or container, such as a sharps container.

In one embodiment, the inner shield can be inserted into an opening forming a well in the apparatus to engage a gripping member within the apparatus so that the inner shield is retained by a friction fit or interference fit. The needle hub and cannula can then be pulled away to separate the inner shield while the inner shield is retained in the well without the need for the user to handle the inner shield. The inner shield can be pushed past the gripping member to pass into a cavity or tray in the apparatus that forms a sharps container.

One aspect is to provide an apparatus or device for receiving and supporting a pen needle assembly to attach the needle hub to the delivery device without the need for the user to handle the exposed hub with the exposed cannula on the needle hub. The needle hub assembly is positioned in the apparatus so that the delivery device can be attached to the non-patient end of the needle hub. An inner needle shield on the needle hub can then be inserted into an opening in the device to grip the inner shield by an extraction mechanism so that the inner shield can be separated from the needle hub without handling the inner shield. After use, the needle hub is positioned in the outer cover that is retained in an opening of the device and disconnected from the delivery device where the device retains the used needle hub and outer cover.

The apparatus includes a housing having an internal cavity for receiving and storing used pen needle assemblies and the associated components. The housing has a gripping mechanism with at least one gripping member, such as a movable jaw, that is able to grip the outer cover of a pen needle assembly so that the needle hub can be attached to the delivery pen. The used needle hub can be inserted back into the outer cover that is retained in the apparatus and separated from the delivery pen. An actuator can be actuated to release the outer cover so that the outer cover and used needle hub can be removed from the apparatus or deposited directly into a storage compartment in the device for storing used pen needle assemblies until ready for disposal.

A pen needle apparatus in one aspect comprises a housing, a movable gripping assembly, and an actuator. The housing has an inner cavity, a top end, and a bottom end. The movable gripping assembly is configured for gripping an outer cover of a pen needle assembly when the gripping assembly is in a first closed position and for releasing the outer over when the gripping assembly is in a second open position. The actuator is connected to the housing and the movable gripping assembly to move the gripping assembly between the first position and the second position to release the outer cover.

The gripping assembly in one embodiment includes at least one and typically two movable jaws that can grip and retain the outer cover and can move away from each other to release the outer cover. In one embodiment, the jaws slide in a substantially linear direction away from each other. The assembly includes the actuator such as a movable cover that can include a mechanism to separate and move the jaws outwardly in a linear direction to release the outer cover. The actuator can have a slot forming a cam surface that cooperates with a cam follower on the jaws so that movement of the actuator imparts linear movement to the jaws to enable the jaws to reciprocated between an open position and closed position. The jaws and the actuator can be spring biased in one embodiment to return the jaws and actuator to the starting position.

The features are further provided by a pen needle assembly apparatus for receiving a pen needle assembly, where the apparatus includes a housing, a movable gripping assembly, and an actuator. The housing has an inner storage compartment, an open top end configured for receiving a pen needle assembly, a bottom end, and an opening for engaging an inner shield of the pen needle assembly for removing the needle hub from the outer cover. The movable gripping assembly is coupled to the housing and oriented with respect to the open top end. The gripping assembly is configured for gripping the outer cover of the pen needle assembly in a first position, and being movable to a second position to release the outer cover. The actuator is coupled to the housing and the gripping assembly for moving the gripping assembly between a first gripping position and a second releasing position with respect to the outer cover.

After use of the needle hub and cannula, the needle hub while attached to the delivery pen is inserted into the opening and into the outer cover where the needle hub can be gripped by a friction fit or interference fit to the outer cover so that the pen needle delivery device can be separated from the needle hub without the operator handling the needle hub thereby reducing the risk of inadvertent needle stick.

The features of the apparatus are further attained by a method of coupling the needle hub of a pen needle assembly to a delivery device using a pen needle assembly apparatus. The apparatus has a top wall with an opening and a gripping assembly supporting the pen needle assembly, and an actuator to operate the gripping assembly. The method includes the steps of inserting the coupling end of the delivery device into a pen needle assembly that is retained by the gripping assembly and coupling to the open end of the needle hub. The delivery device with the needle hub attached is removed leaving the outer cover retained by the gripping assembly. The inner shield is inserted into an opening or well where the inner shield is gripped with sufficient force that the needle hub can be pulled free and separated from the inner shield to expose the cannula for use in delivering the substance to the patient. After use, the needle hub is inserted into the outer cover that was retained in the first well and disconnected from the delivery device. The actuator is then actuated to release the used needle hub and outer cover from the gripping assembly.

The objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 1 is an exploded perspective view of a pen needle delivery device in one embodiment showing the pen needle assembly that includes a needle hub supporting a cannula, inner shield, and outer cover;

FIG. 2 is a cross-sectional view of the pen needle assembly;

Throughout the drawings, like reference numbers will be understood to refer to like parts, components, and structures.

DETAILED DESCRIPTION OF THE EXEMPLARY EMBODIMENTS

Figure 3:
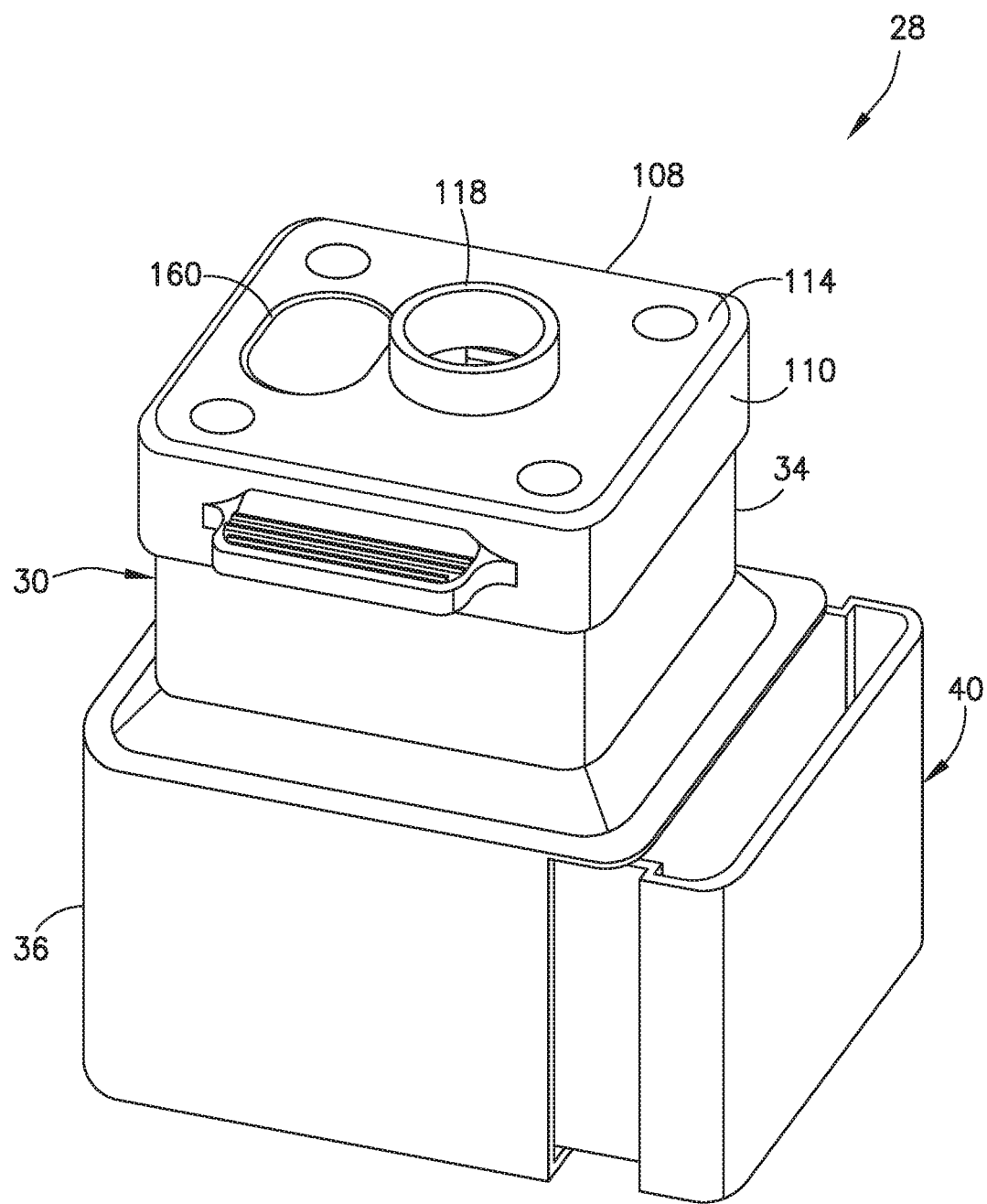
FIG. 3 is a perspective view of the apparatus and storage device in one embodiment of the invention.

The present invention is directed to a pen needle assembly apparatus for storing and supporting at least one and preferably a plurality of pen needle assemblies for use with a pen delivery device. The invention is further directed to a storage device for a used needle hub where the used needle hub can be replaced in the device after use and later discarded without handling the needle hub to reduce the risk of accidental needle stick.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. The exemplary embodiments are presented in separate descriptions, although the individual features and construction of these embodiments can be combined in any number of ways to meet the therapeutic needs of the user.

It will be understood by one skilled in the art that this disclosure is not limited in its application to the details of construction and the arrangement of components set forth in the following description or illustrated in the drawings. The embodiments herein are capable o of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are employed to aid illustration, but are not limiting.

The apparatus for the needle hub assemblies can enable the convenient and easy assembly and removal of the needle hub on the pen delivery device with reduced handling of the exposed needle cannula. The device for the needle hub assemblies can be placed on a flat surface, such as a table, so that the pen needle delivery device can be attached to the needle hub assembly with one hand thereby reducing the risk of the needle stick by handling the needle hub with the exposed needle cannula.

Pen needle delivery device 10, as shown in FIG. 1 typically comprises a dose knob/button, an outer sleeve 12, and a cap. A dose knob/button allows a user to set the dosage of medication to be injected. The outer sleeve 12 is gripped by the user when injecting medication. The cap is used by the user to securely hold the pen injector device 10 in a shirt pocket or other suitable location and provide cover/protection from accidental needle injury.

In standard pen needle delivery devices the dosing and delivery mechanisms are all found within the outer sleeve 12 and is not described in greater detail here as they are understood by those knowledgeable of the prior art. A medicament cartridge is typically attached to a standard pen injector housing by known attachment means. The distal movement of a plunger or stopper within the medicament cartridge causes medication to be forced into the reservoir housing. The medicament cartridge is sealed by a septum and punctured by a septum penetrating needle cannula located within a reservoir or housing. Reservoir housing is preferably screwed onto the medicament cartridge although other attachment means can be used. The pen needle delivery device can be a standard pen delivery device known in the industry so that the pen needle delivery device is not shown in detail. The pen needle assembly 18 as shown in FIG. 2 includes a needle hub 16 supporting a cannula 20, an outer cover 22, and an inner shield 24. A protective seal 26 is attached to the open end of the outer cover as shown in FIG. 2 to enclose the needle hub and cannula to maintain a clean and sterile condition. The seal 26 can be a label or other closure member that can be easily peeled from the outer cover to access the needle hub during use.

The pen needle delivery device 10 is connected to needle hub 16 shown in FIG. 1 that has a connecting non-patient end with internal threads that screw onto a threaded end 18 of the delivery device 10. The needle cannula 20 extends from the patient end of the needle hub 16 for delivering the substance to the patient. The outer cover 22 can be provided to cover the needle cannula to protect the patient from accidental needle stick before and after use. The outer cover 22 includes ribs 23 to assist in gripping the outer cover during use. The inner shield 24 is provided over a post extending from the end of the needle hub 16 to enclose the cannula. During use, the needle hub 16 is connected to the pen delivery device and the inner shield is removed. After use, the outer cover is generally placed back on needle hub to cover the needle cannula. The needle hub with the cover is then removed from the pen needle delivery device and discarded.

The apparatus 28 is configured for receiving and supporting at least one pen needle assembly 18 in a position where the delivery device 10 can be coupled to the needle hub 16 for use for injecting the substance to the patient without the need for the user to handle the needle hub 16 with the exposed cannula. The used needle hub 16 and cannula 20 can then be positioned back into the outer cover 22 that is retained in the apparatus and separated from the delivery device. The used outer cover and needle hub and the inner shield are retained in the device.

An apparatus 28 is provided for receiving a pen needle assembly 18 for coupling the pen needle hub 16 to the delivery pen and for separating the pen needle hub from the delivery pen after use. In one embodiment, the apparatus 28 includes a housing 30 and a retaining and gripping assembly 32 within the housing, and an actuator 108. The housing 30 as shown in FIG. 3 has a top end 34 and a bottom end 36. Bottom end 36 has a bottom face with a non-slip surface. The nonslip surface can be molded directly onto the bottom face or can be a nonslip material, such as an elastomeric material, applied to the bottom surface to retain the housing in a stable position during use on a table or other flat surface.

Figure 4:
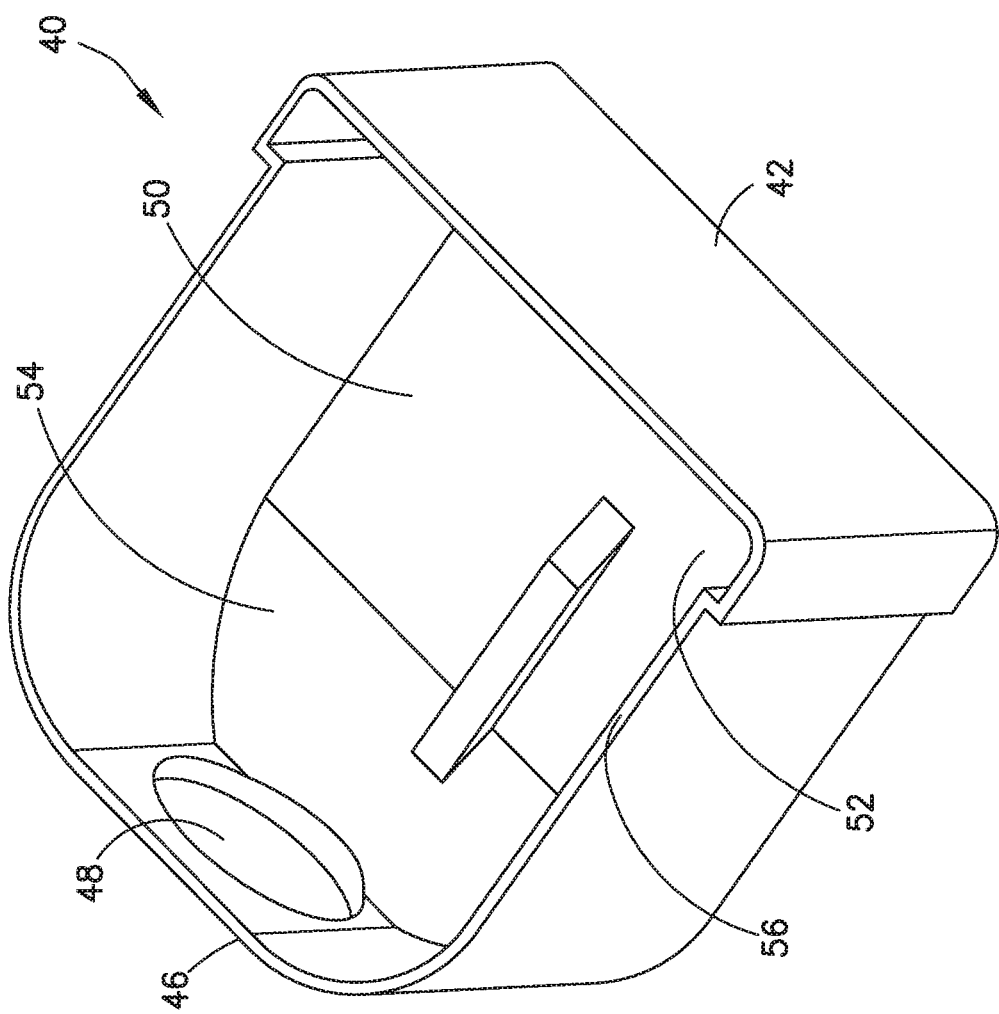
FIG. 4 is a perspective view of the storage tray in one embodiment.

The bottom end 36 of housing 30 has an inner cavity 38 with a dimension sufficient to retain and store a plurality of used pen needle assemblies. In the embodiment shown, a tray 40 is provided to slide within the inner cavity 38 defining a receptacle or sharps container for the used pen needle assemblies. In the embodiment shown in FIG. 4, tray 40 has a front wall 42, sidewalls 44, and a rear wall 46 with an opening 48. Tray 40 has a bottom wall 50 having a first section 52 adjacent the front wall 42 and a second inclined section 54 converging upward from the first section 52 to the opening 48 in the rear wall 46. Tray 40 has an open top end 56 at a lower end of the upper section of the housing 30. Tray 40 can be constructed for single use or can be reusable.

Figure 5:
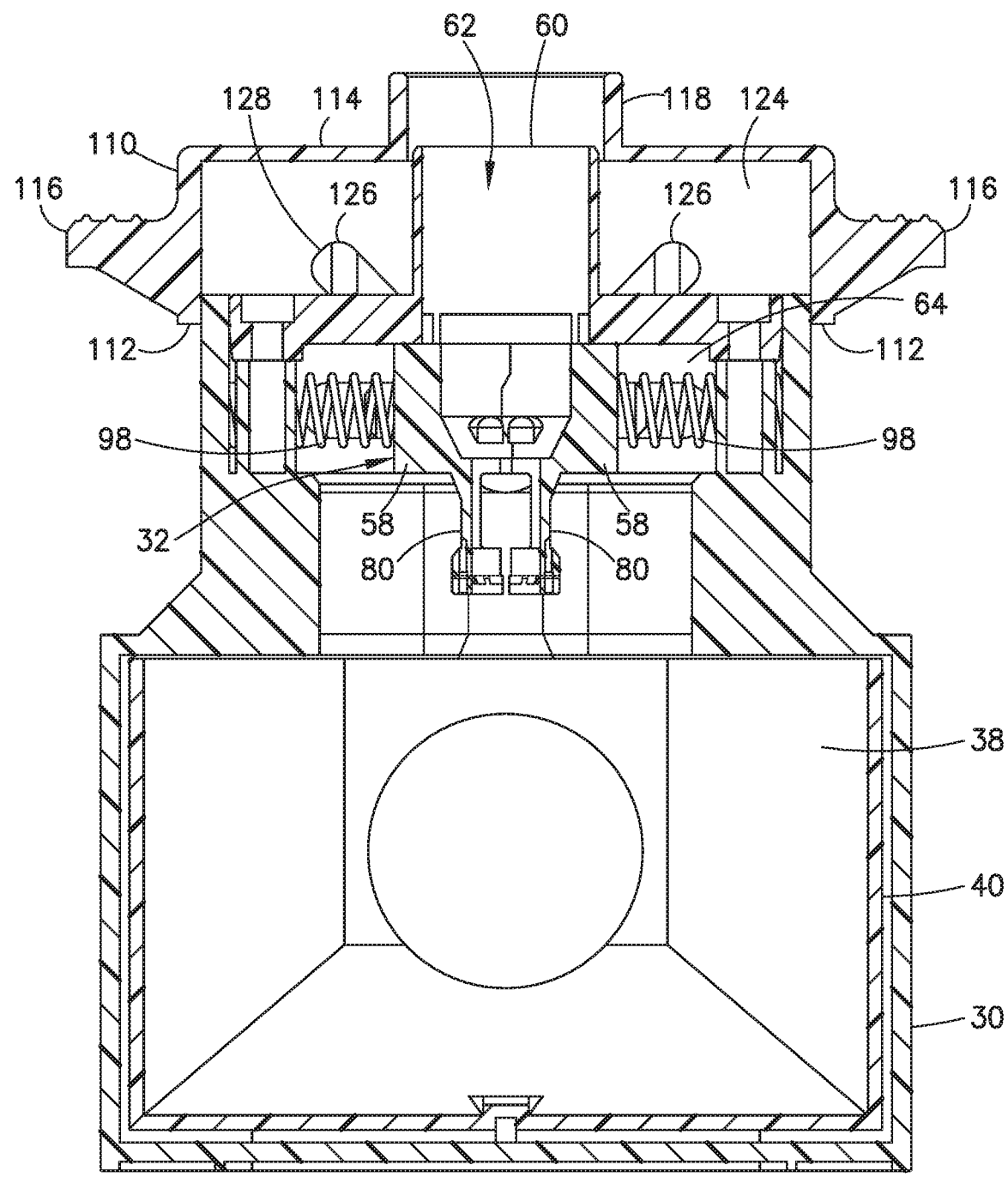
FIG. 5 is a cross sectional view of the apparatus of FIG. 3 showing the gripping assembly.
Figure 6:
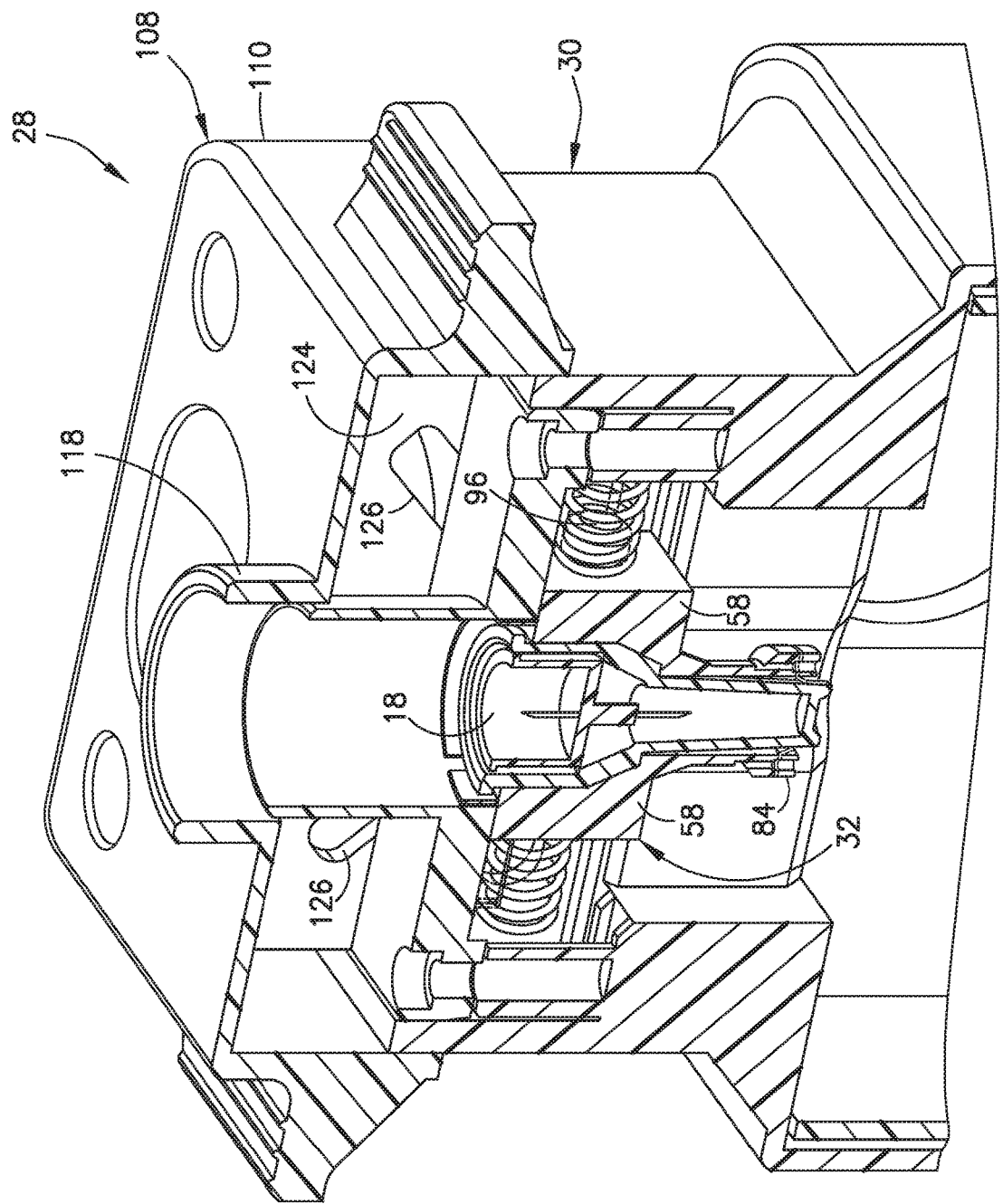
FIG. 6 is a partial cross-sectional view of the apparatus and pen needle assembly.

Referring to FIGS. 5 and 6, the gripping assembly 32 is provided for supporting and gripping a pen needle assembly for connecting the needle hub 16 to the delivery pen and disconnecting the needle hub from the delivery pen after the use. The gripping assembly 32 is a movable assembly that can move between a first position for engaging and gripping the outer cover the pen needle assembly and a second position for releasing the outer cover.

Figure 14:
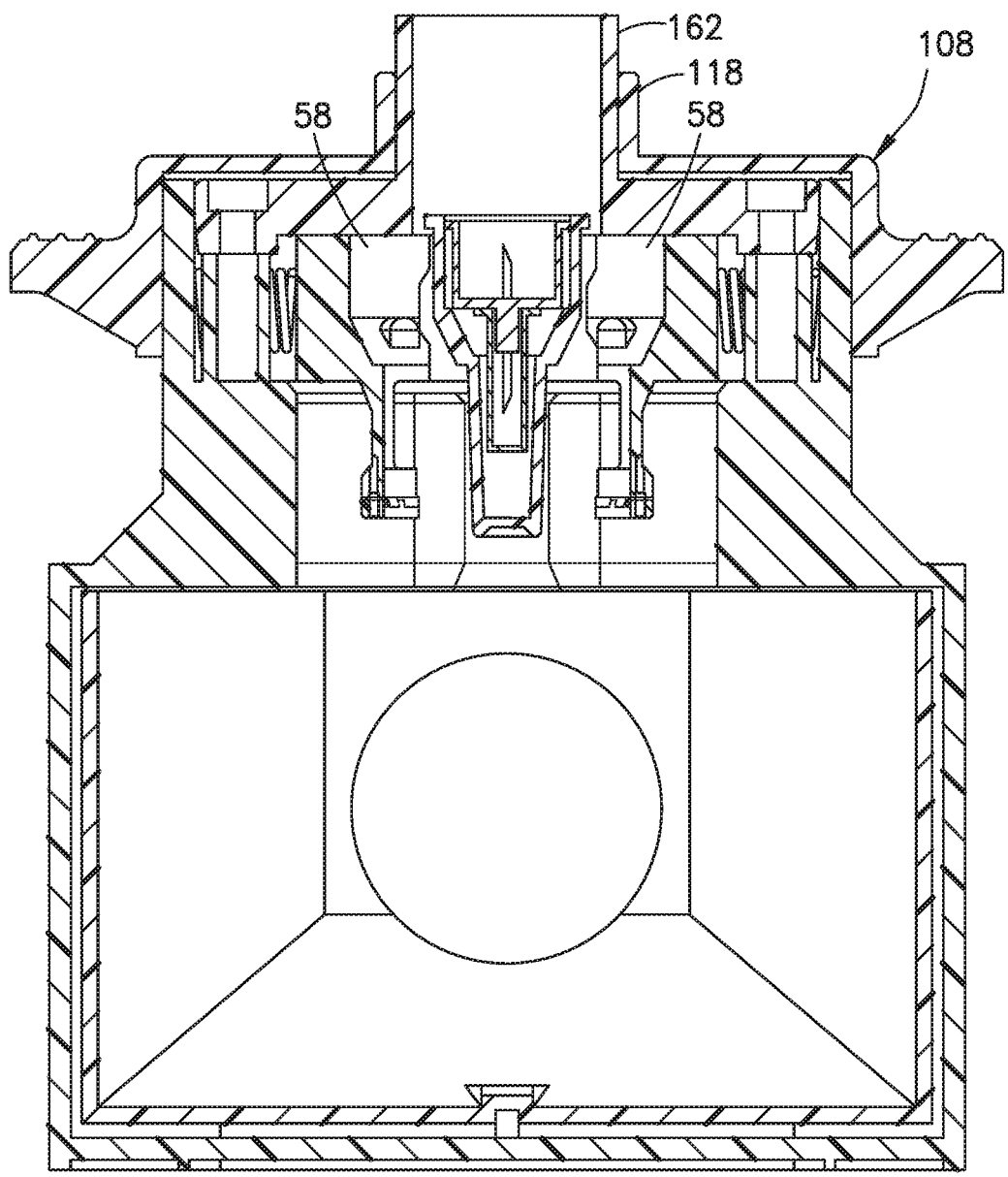
FIG. 14 is a cross-sectional view showing the actuator moving the jaws of the gripping mechanism to release the pen needle assembly.

In the embodiment shown, the gripping assembly 32 includes two opposing jaws 58 that are movable between a first closed position shown in FIGS. 5 and 6 and a second open position shown FIG. 14. The jaws 58 in one embodiment move in a substantially linear direction between the first position and the second position. The housing 20 has a collar 60 extending from the top end of the housing to define an opening 62 or well with a dimension complementing the outer dimension of the pen needle assembly so that the pen needle assembly can slide through and into contact with the gripping assembly with the gripping assembly 32. The housing 20 is an inner cavity 64 for receiving the movable jaws 58.

Figure 7:
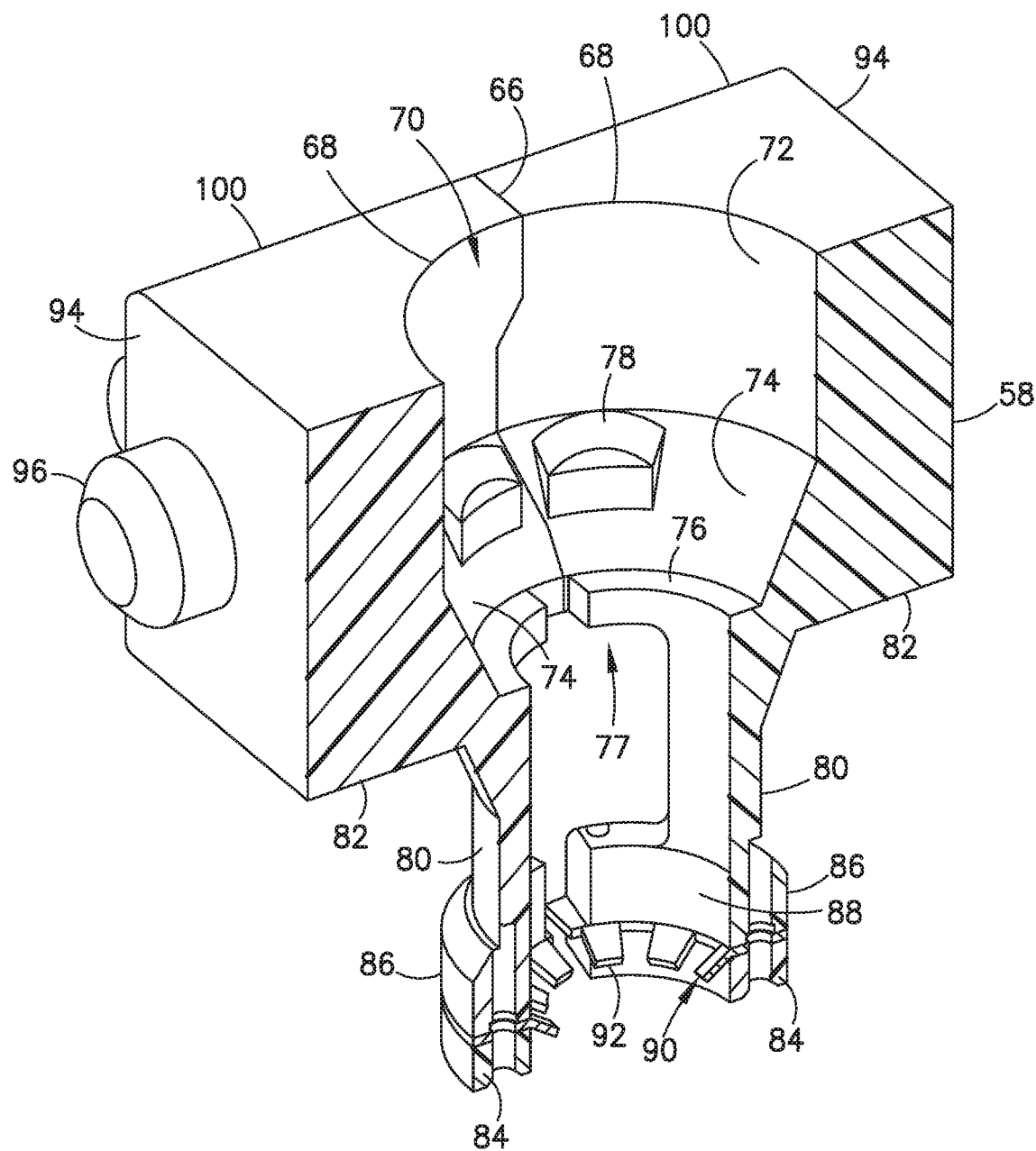
FIG. 7 is a partial cross-sectional view of the gripping assembly formed by the jaws in one embodiment.

Jaws 58 of the gripping assembly 32 as shown FIG. 7 are substantially mirror images of each other and configured for sliding between the closed position shown in FIG. 7 and the open position shown in FIG. 14. Jaws 58 have an inner mating surface 66 with a substantially semicircular open concave area 68 where the open concave area 68 of each jaw 58 defines a substantially circular shaped well 70 or opening in the gripping assembly 32 for receiving a pen needle assembly. As shown in FIG. 7, the concave area 68 has a substantially straight portion 72 extending in a longitudinal direction with respect to a longitudinal center axis and forming a side wall of the well 70. A bottom section of the well 70 is formed by an inclined section 74 with an inwardly extending lip 76 forming a bottom opening 77 having a dimension less than the opening at the top end face of the gripping assembly 32 formed by jaws 58. The inclined section 74 is provided with one or more projecting detents 78 to engage the ribs 23 on the outer cover of the pen needle assembly to resist rotation of the outer cover with respect to the gripping assembly 32.

A leg 80 extends from a bottom side 82 of each jaw 58 that extends outwardly a distance to complement the longitudinal dimension of the outer cover of the pen needle assembly. The leg 80 has a distal end formed by a semicircular portion 84 with a convex outer surface 86 and a concave inner surface 88. The inner surface 88 is provided with a gripping member 90 for gripping the outer surface of outer cover 22 of the pen needle assembly. In the embodiment shown, the gripping member 90 can be a spring clip including a plurality of teeth 92 encircling the open bottom end of jaws 58. In the embodiment shown, the teeth 92 are provided at an inclined angle projecting toward the center axis of the jaws 58 and extending away from the main body portion of the jaws. The gripping member 90 can be integrally formed with the end portion 84 or can be a separate member attached to the end portion 84. The gripping member 90 can be made of plastic, metal, or other suitable material. The gripping member 90 can be a metal spring clip that can have sharp edges to engage the outer cover and resist rotation until released by the gripping assembly.

Figure 15:
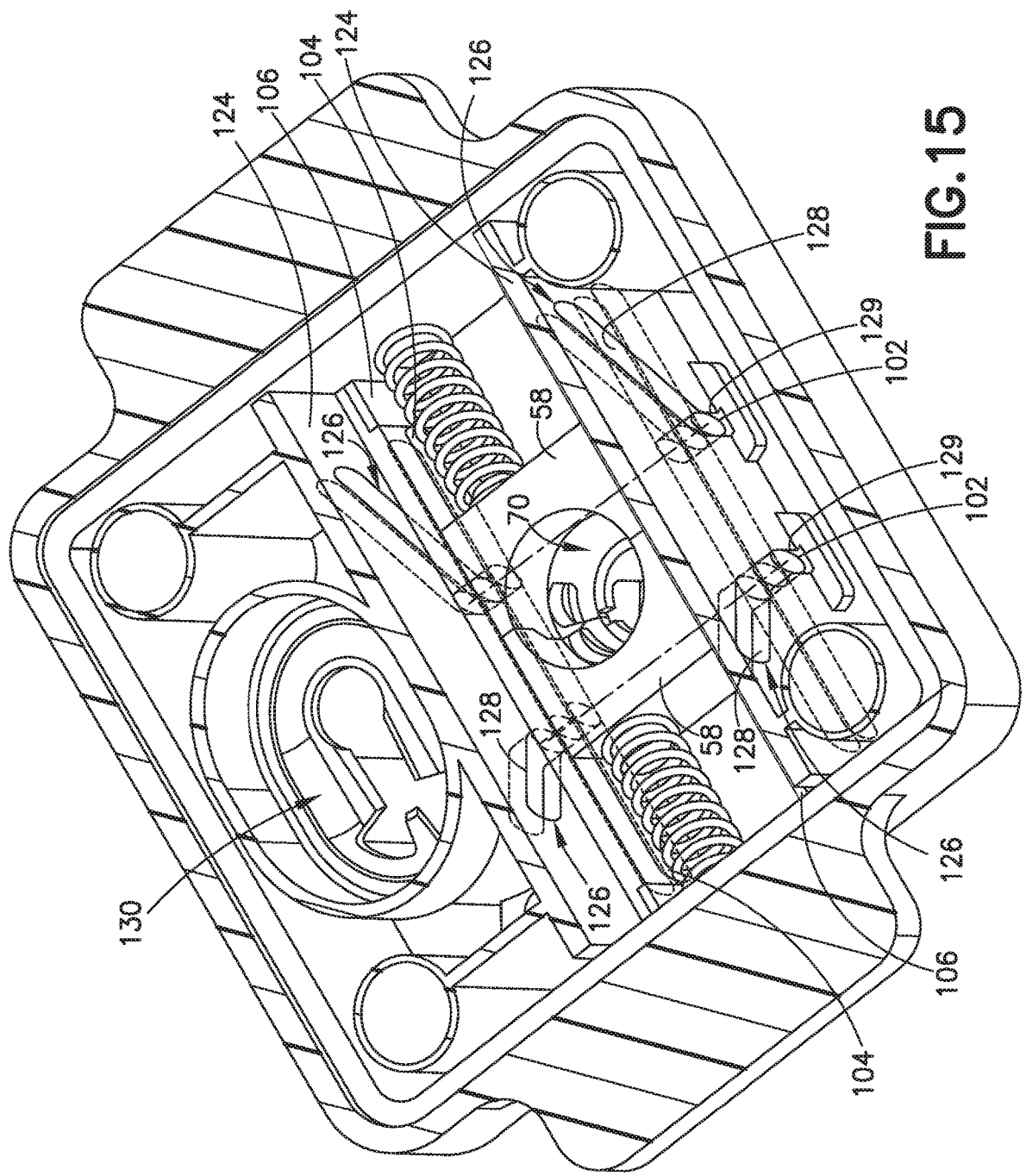
FIG. 15 is a partial cross sectional side view showing the actuator in a first extended position with the movable jaws of the gripping mechanism in the closed position.
Figure 16:
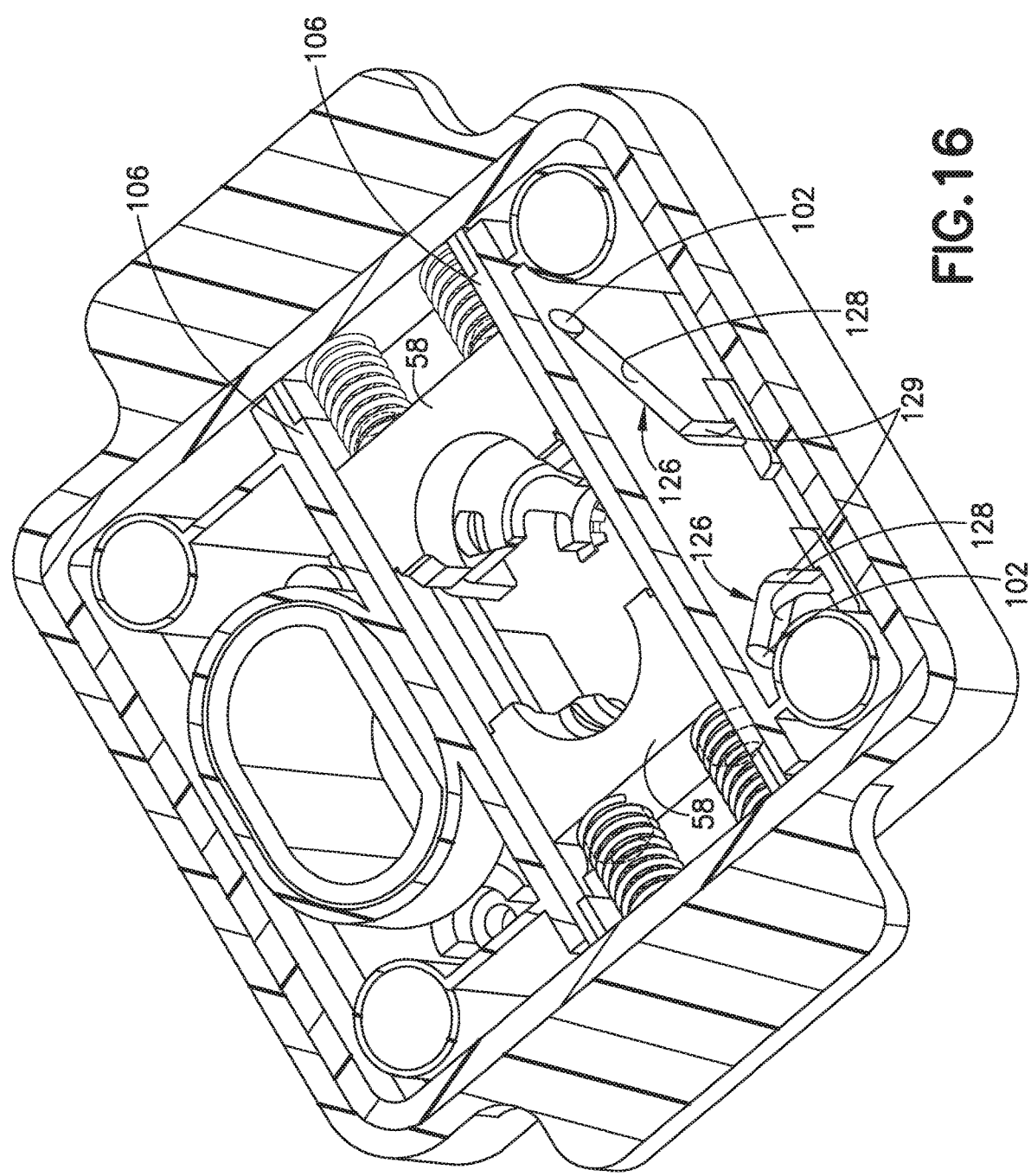
FIG. 16 is a partial cross sectional side view showing the actuator in the actuating position to move the jaws to the open position to release the pen needle assembly.

Jaws 58 have an end face 94 with a protruding member 96 for supporting a spring 98. Spring 98 or other biasing member is provided between an inner wall of housing 30 and the respective jaw to spring bias the jaws 58 toward each other to the closed position. In one embodiment, spring 98 is a coil spring. The outer side faces 100 of the jaws 58 include a projecting member forming a cam follower 102 as shown FIGS. 15 and 17. In the embodiment shown, spring 98 is a coil spring extending between the respective end face 94 and an inner wall of the housing 30 to bias the jaws toward each other. The housing 30 includes inner side walls 106 having a slot 104 to enable the jaws 58 to slide in a substantially linear direction between a closed position and an open position. The cam follower 102 extending from the side faces 100 of the respective jaw extends through the slot 104 in inner side walls 106 as shown in FIGS. 15 and 16. The slot 104 in the embodiment shown extends in a direction substantially perpendicular to the longitudinal or axial direction of the housing and the gripping assembly 32.

The actuator 108 in the embodiment shown defines a cover coupled to the housing 30. The actuator 108 is coupled to the housing for movement to actuate the jaws 58 and move the jaws between the closed position and the open position. In the embodiment shown, the actuator 108 slides over the outer surface of the housing between an extended position shown in FIG. 5 and an actuated position shown in FIG. 14.

Figure 10:
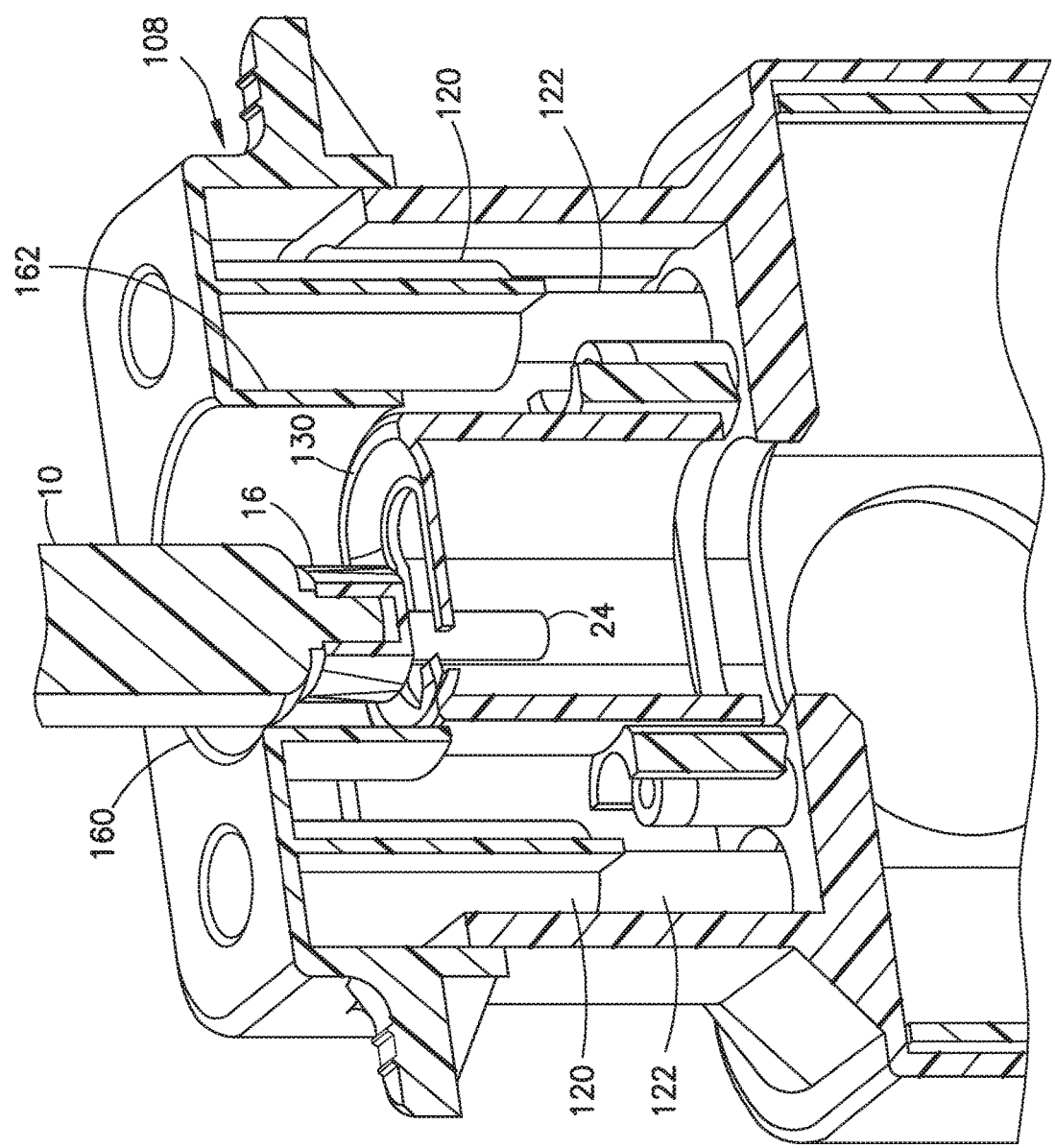
FIG. 10 is partial cross-sectional view of the pen needle delivery device inserting the inner shield into an extractor mechanism in the well of the device.

Actuator 108 forming the cover as shown in FIG. 3 has a sidewall 110 complementing the outer dimension of the housing, an open bottom end 112, and a top wall 114. Side wall 110 includes outwardly projecting tabs 116 for assisting in manipulating the actuator 108 relative to the housing 30. Top wall 114 has a collar 118 defining an opening for receiving the pen needle assembly. Collar 118 has an inner surface with a shape and dimension complementing the outer shape and dimension of the collar 60 of the housing so that the collar 118 slides over the collar 60 of the housing during the reciprocating movement of the actuator with respect to the housing. The actuator 108 is shown as a movable cover and is provided with downwardly extending channels 120 that receive a respective cylindrical pin 122 extending upwardly within the housing to assist in guiding the actuator 108 relative to the housing as shown in FIG. 10.

Actuator 108 includes a substantially planar plate 124 as shown in FIGS. 15 and 16 positioned on each opposite side of the jaws 58 and walls 106 for coupling to the jaws and moving the jaws between the open position and closed position. The plates 124 are fixed to the actuator 108 and slide with actuator 108 during movement of the actuator. In one embodiment of the invention, each plate 124 includes two slots 126 defining a cam surface 128 that are inclined with respect to a direction of travel of the actuator. The slots 126 as shown are inclined with respect to each other and converge toward each other at a center of the lower end of the respective plate 124.

In the embodiment shown, a plate 124 is associated with the two opposite sides of the jaws to provide a smooth operation and movement. In other embodiments, a single plate or other cam mechanism can be provided. As shown in FIG. 15, the lower end of the slots 126 include a bottom section 129 extending in a vertical direction substantially parallel to the longitudinal direction of the housing and parallel to the direction of travel of the actuator.

The cam follower 102 of the respective jaw 58 extends through the slot 104 formed in the inner wall 106 of the housing 30 and into the slot 126 of the plate 124. The downward movement of the actuator 108 relative to the housing causes the inclined cam surfaces 128 to slide the jaws 58 apart. As shown in FIG. 15, the actuator 108 is in a first position extending from the housing. The cam follower 102 is received in the respective slot 126 and positioned at a bottom end of the respective slot where the jaws 58 are in the closed position as shown in FIG. 15. A downward movement of the actuator 108 enables the cam surfaces 128 in the plate 124 to move the cam follower 102 and the respective jaws 58 away from each other as shown FIG. 16. The springs 98 bias the jaws 58 together to the closed position and return the plates and actuator to the original position. In other embodiments, a spring or other suitable biasing member is provided in the housing to return the actuator 108 to the original position shown in FIG. 15.

Figure 11:
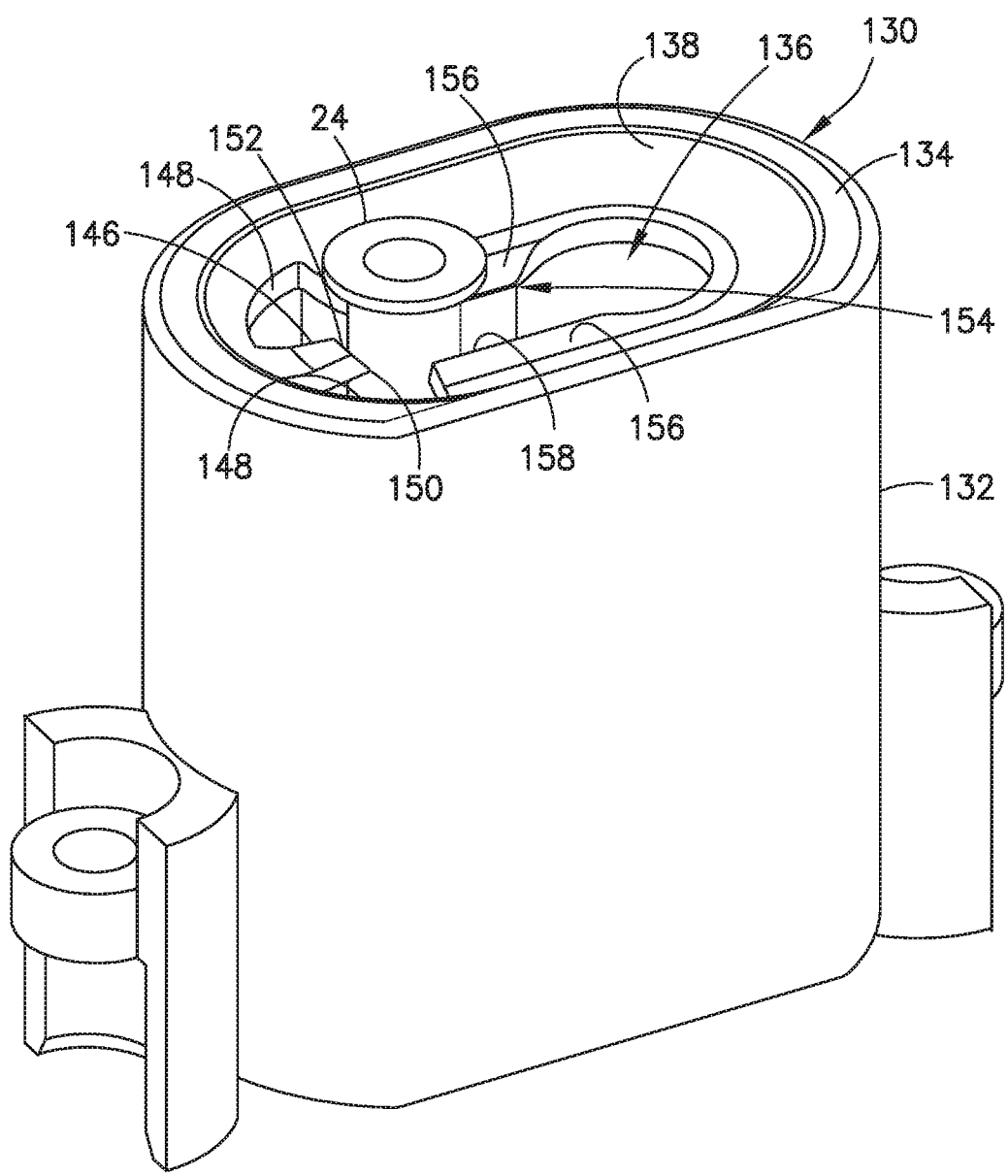
FIG. 11 is a top perspective view of the extractor mechanism for separating the inner shield from the needle hub.

Housing 30 includes an extractor mechanism 130 to assist in removing the inner shield 24 of the pen needle assembly without the need for the patient to handle the inner shield. As shown in FIGS. 10 and 11, the extractor 130 includes a side wall 132 defining a passage between the open top end of the housing and the cavity of the bottom end. The extractor 130 can be formed from a sheet metal clip attached to the side wall 132 where the clip includes sharp edges to engage the inner shield. A top wall 134 includes a substantially keyhole shaped slot 136. In the embodiment shown, top wall 134 has a concave surface 138 to assist in guiding the inner shield 24 into the slot 136. The key hole shaped slot 136 has an enlarged, substantially circular opening 140 and a longitudinally extending opening 142 having a width less than the diameter of the circular opening 140. The circular opening 140 has a dimension slightly larger than the outermost dimension of the inner shield 24 so that the inner shield can pass through without interference.

Figure 8:
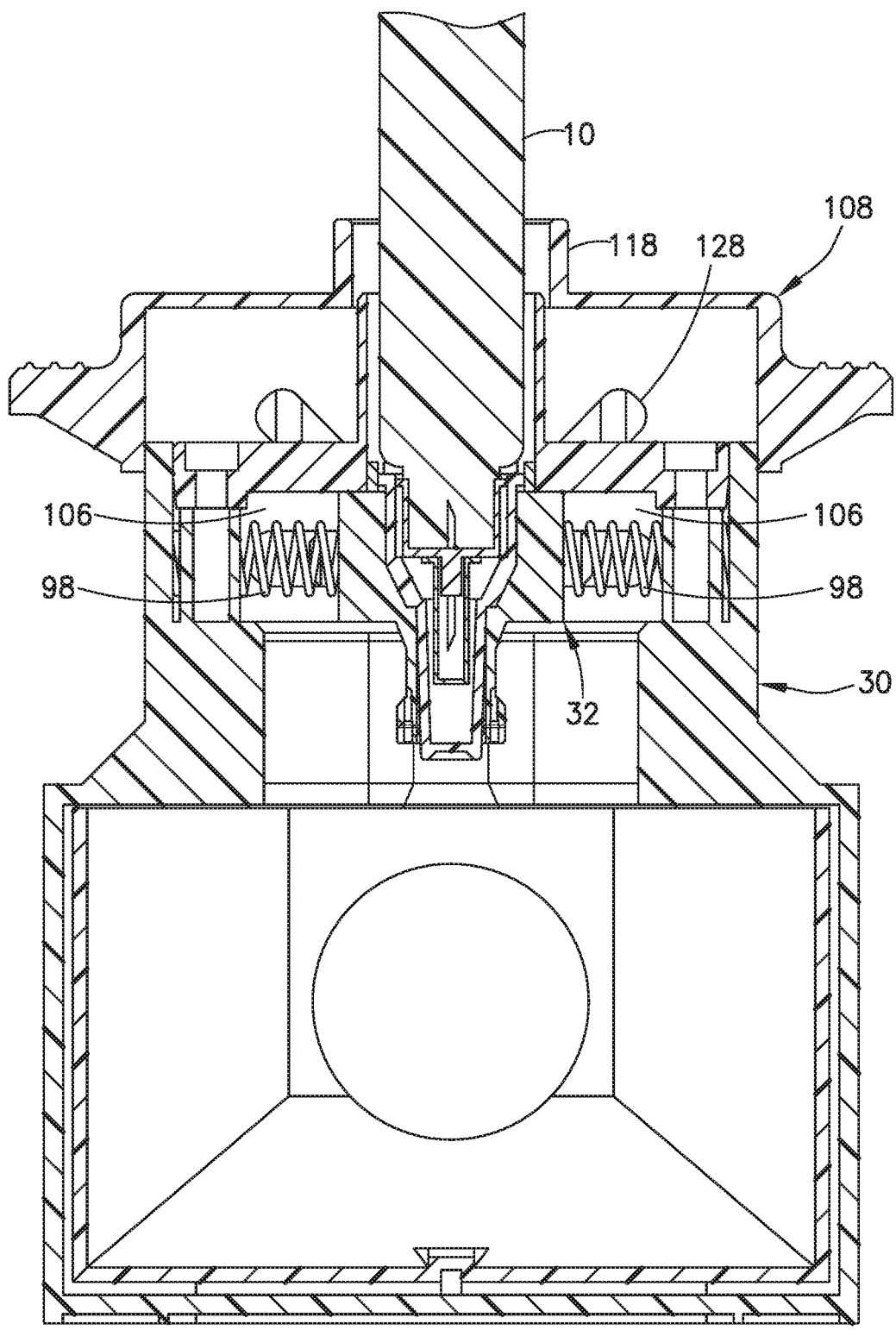
FIG. 8 is a cross-sectional view of the apparatus showing the delivery device being connected to the needle hub.

The distal end 144 of the longitudinal portion 142 includes at least one tooth 146 projecting inwardly with respect to the circular opening 140 and defining recessed areas 148. The tooth 146 in the embodiment shown is formed with an inclined surface forming a sharp tip 150. In the embodiment shown, the inclined surface 152 is inclined in a generally downward direction to allow the inner shield 24 to slide over the tip and resist removal of the inner shield in an upward direction. Tooth 146 is sufficiently flexible so that the inner shield can be pushed through the opening to pass into the tray or other receptacle in the housing. The inner longitudinal edges 154 of the longitudinal slot 142 are formed with an inclined surface 156 that converge to a sharpened edge 158. The inclined surfaces 156 are inclined downwardly toward the bottom end of the housing to assisting gripping the inner shield during use of the device. The actuator 108 forming the cover of the housing includes an opening 160 with a downwardly extending collar 162 extending from an inner edge of the opening 160. As shown in FIG. 8, the collar 162 has a dimension complementing the outer dimension of the sidewall 132 of the extractor 130 so that the collar 162 slides over the extractor during use.

The assembly is able to receive a pen needle assembly to assist the user in attaching the hub to the delivery pen without the need for the user to handle the needle hub and exposed cannula. During use, the label is removed from the outer cover and the pen needle assembly is placed into the collar of the housing 30 so that the pen needle assembly passes downwardly into the open area defined by the jaws 58 as shown FIG. 6. The pen needle assembly is retained by the jaws 58 and the teeth 92 of the legs 80 engaging the outer surface of the bottom outer cover 22. The detent 78 on the inclined surface of the respective jaws engages the ribs on the outer surface of the outer cover to resist rotation of the outer cover relative to the jaws.

Figure 9:
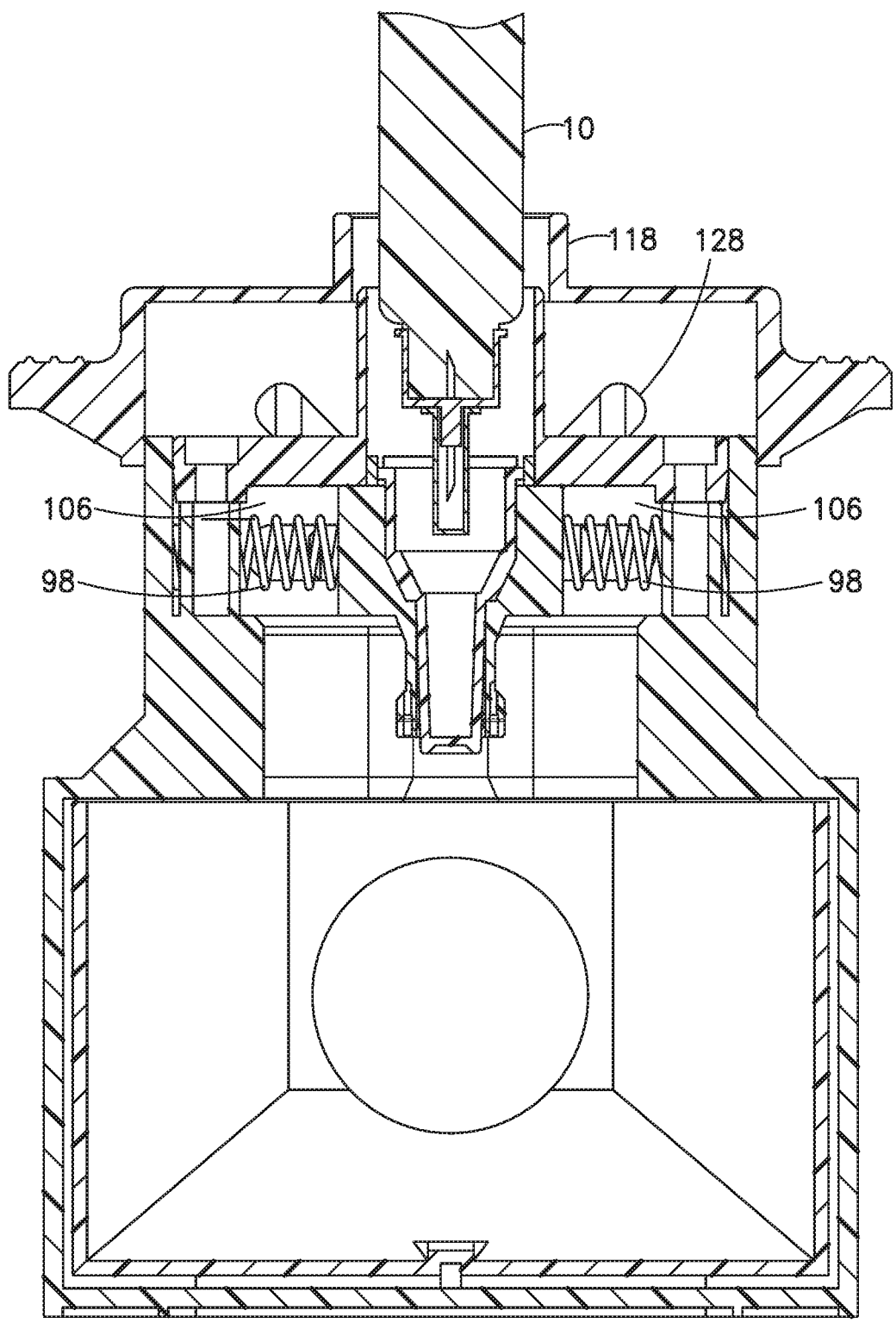
FIG. 9 is a perspective view of the apparatus showing the needle hub being pulled from the outer cover.

As shown in FIG. 8, a delivery pen is then inserted through the opening in the collar 118 of the actuator 108 and the collar 162 on the housing to engage the needle hub of the pen needle assembly. The delivery pen is rotated to engage the internal threads on the needle hub to couple to the delivery pen. As shown in FIG. 9, the delivery pen with the attached needle hub 16 can be retracted from the outer cover 22 leaving the outer cover retained between the jaws 58.

The inner shield 24 is attached to the needle hub 16 to cover the cannula 20 when separated from the outer cover. The delivery pen is then inserted into the extractor 130 as shown in FIGS. 10 and 11 where inner shield 24 passes through the longitudinal slot 142 so that the edges 154 and the tip 150 and engage the outer surface of the inner shield to grip the inner shield and resist upward movement. The delivery pen can then be extracted leaving the inner shield 24 retained in slot 142.

Figure 12:
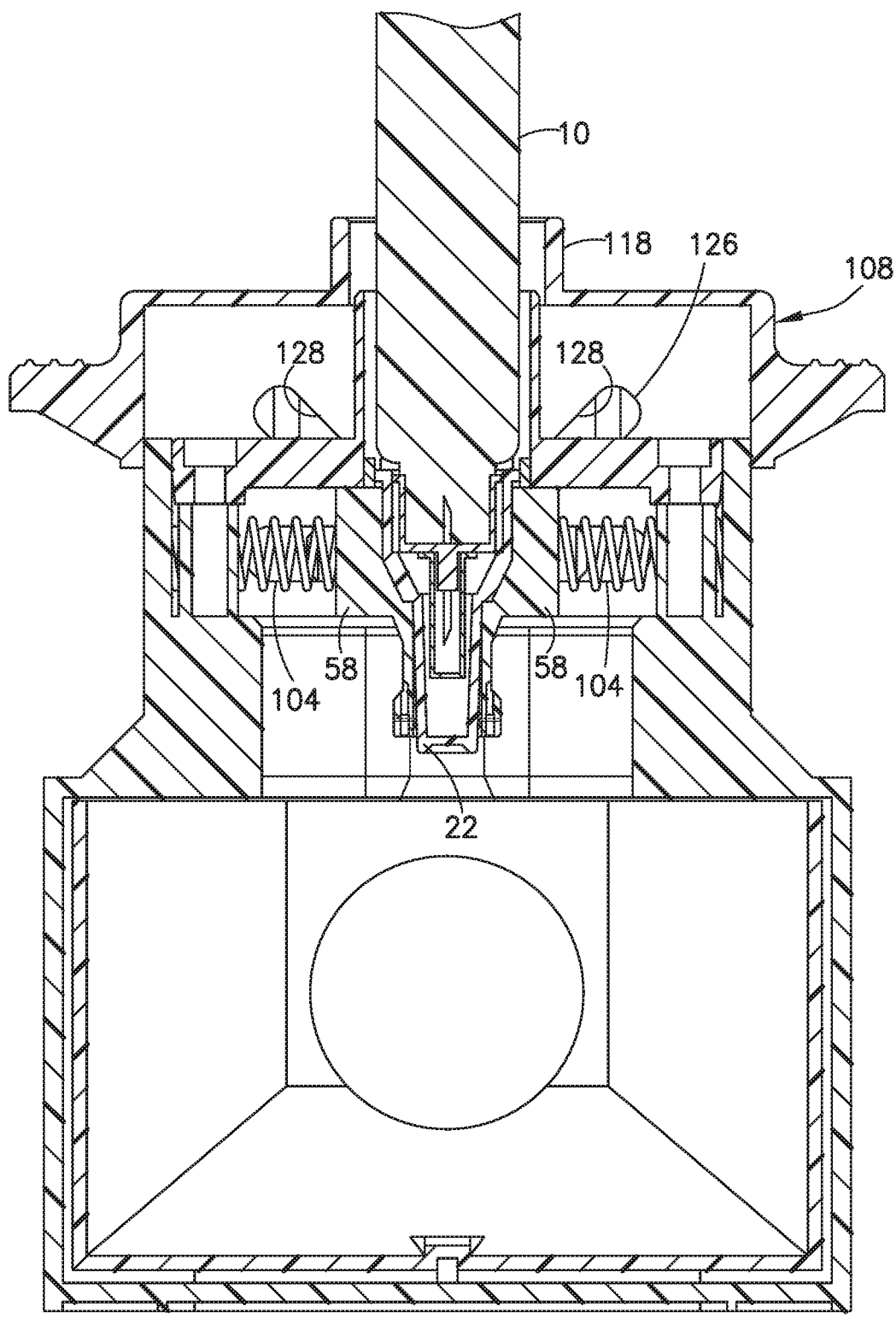
FIG. 12 is a cross-sectional view of the needle hub after use being inserted into the outer cover that is retained in the apparatus.
Figure 13:
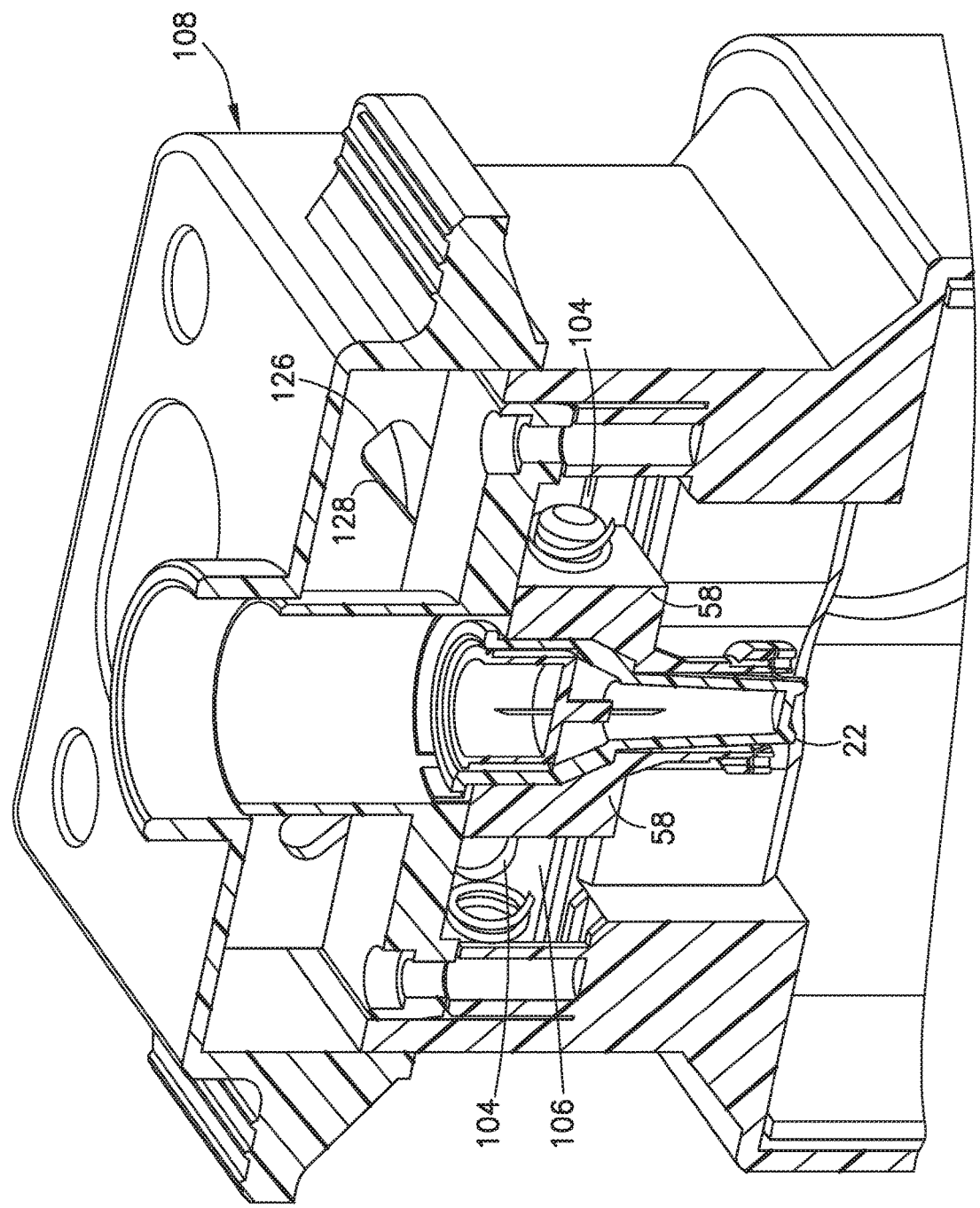
FIG. 13 is a cross-sectional view showing the delivery pen separated from the needle hub and the needle hub positioned within the outer cover after use.

After use of the delivery pen and the pen needle assembly 18, the delivery pen can then be inserted through the collar 162 of the housing as shown in FIG. 12 where the needle hub 16 is again received in outer cover 22 that is retained in the opening between the jaws 58. The delivery pen can then be rotated to disconnect the delivery pen from the internal threads of the needle hub and removed from the apparatus as shown FIG. 13. The actuator 108 can then be depressed to the position shown in FIG. 14 where the cam surfaces 128 engage the respective cam follower 102 on the jaws 58 to move the jaws outwardly in a linear direction to release the outer cover 22 that contains the used needle hub 16. The used outer cover 22 and needle hub 16 are released to pass through the opening into the bottom portion of the housing and into the tray 40 for collecting the used pen needle assembly. The downward force on the actuator 108 is released so that the springs return the actuator 108 to the original position.

The steps can be repeated by placing a new pen needle assembly in the housing and the delivery pen can be attached to the needle hub. As shown in FIG. 15 the new needle hub with the inner shield 24 can be inserted into the opening for the extractor 130 where the tip of the inner shield engages the top end of the previous shield so that a downward force pushes the previous shield past the flexible edges of the tooth 146 and longitudinal edges 154 of the slot 144. The inner shield 24 is then able to drop downward into the tray 40.

Figure 17:
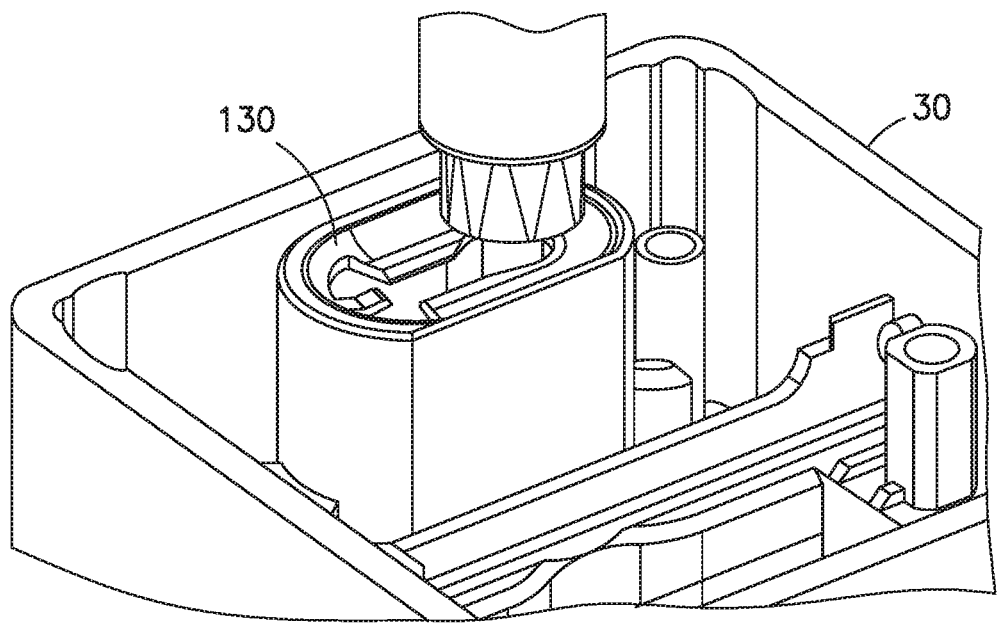
FIG. 17 is a perspective view showing a second inner shield pushing the first inner shield through the opening and into the storage compartment.
Figure 18:
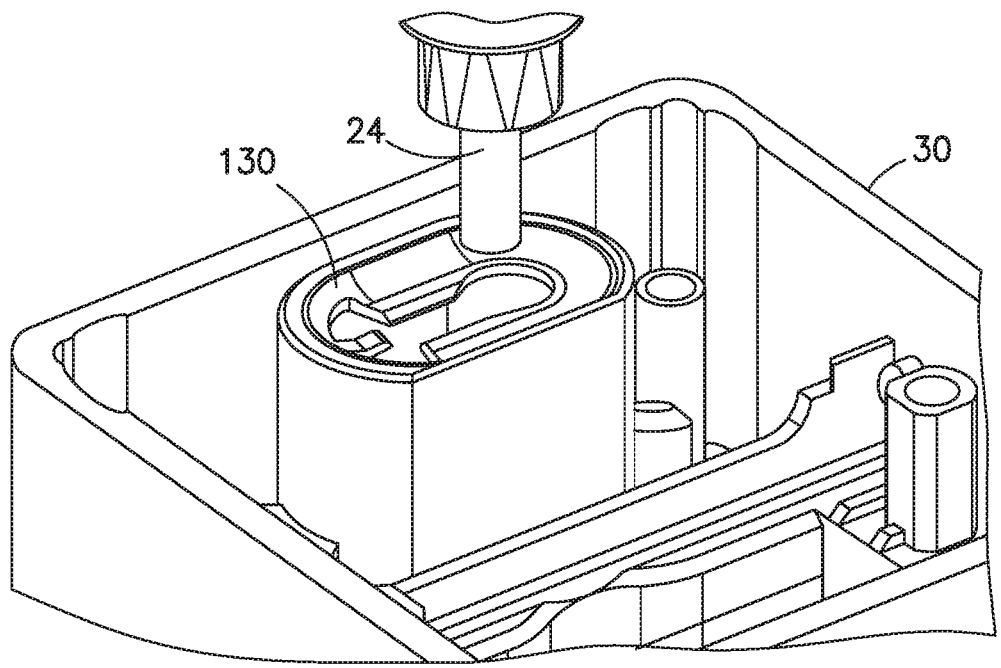
FIG. 18 is a perspective view showing the needle hub being inserted back into the inner shield for later use.
Figure 19:
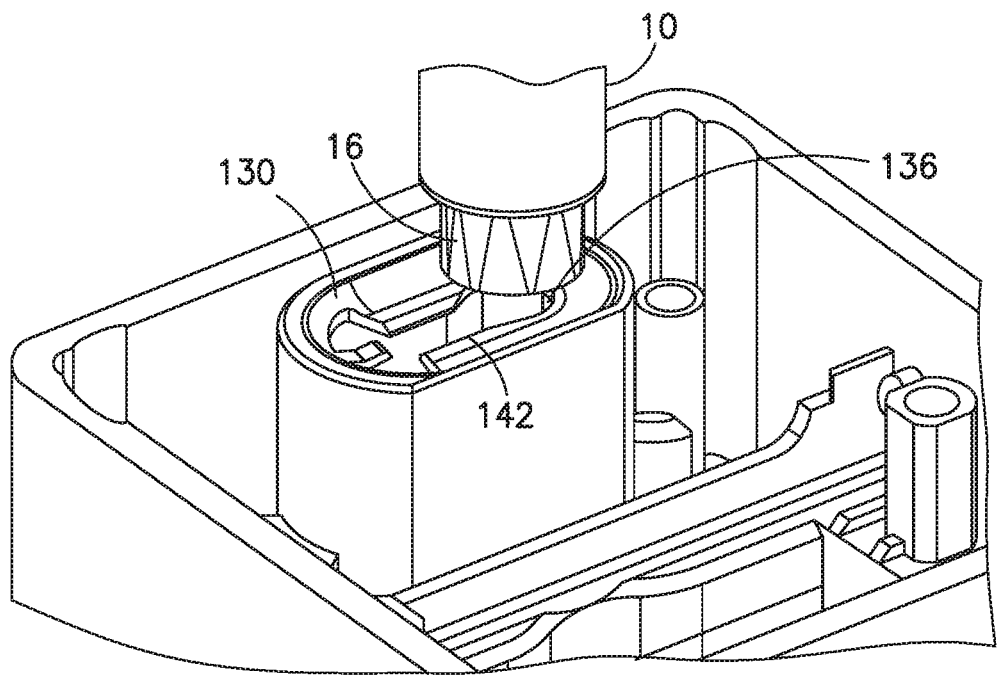
FIG. 19 is a perspective view showing the inner shield sliding to a position for removing the inner shield from the apparatus.
Figure 20:
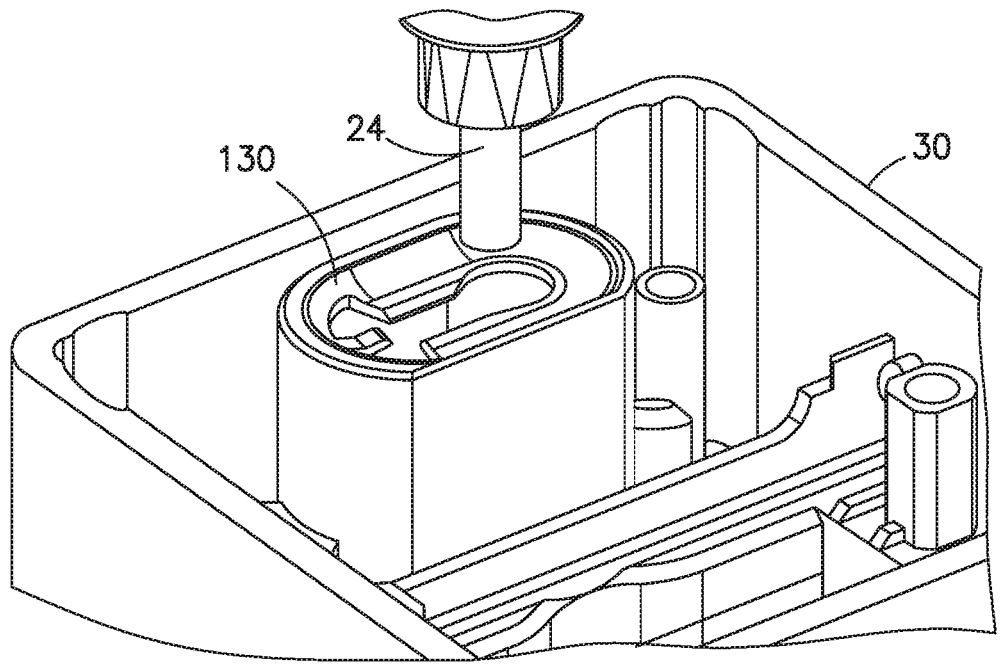
FIG. 20 is a perspective view showing the inner shield removed from the apparatus attached to the delivery pen.

In other embodiments, it may be desirable place the inner shield back onto the needle hub 16 for later use after the delivery device has been prepared for use. As shown in FIG. 17, the inner shield 24 can be placed back onto the post of the needle hub 16 by inserting the delivery pen and needle hub back into the apparatus as shown. The inner shield 24 can then slide along the longitudinal slot 142 to the circular open portion 140 as shown FIGS. 19 and 20 to release the inner shield from the extractor 130. The delivery pen with the needle hub and inner shield 24 attached then can be withdrawn and stored for later use.

Figure 21:
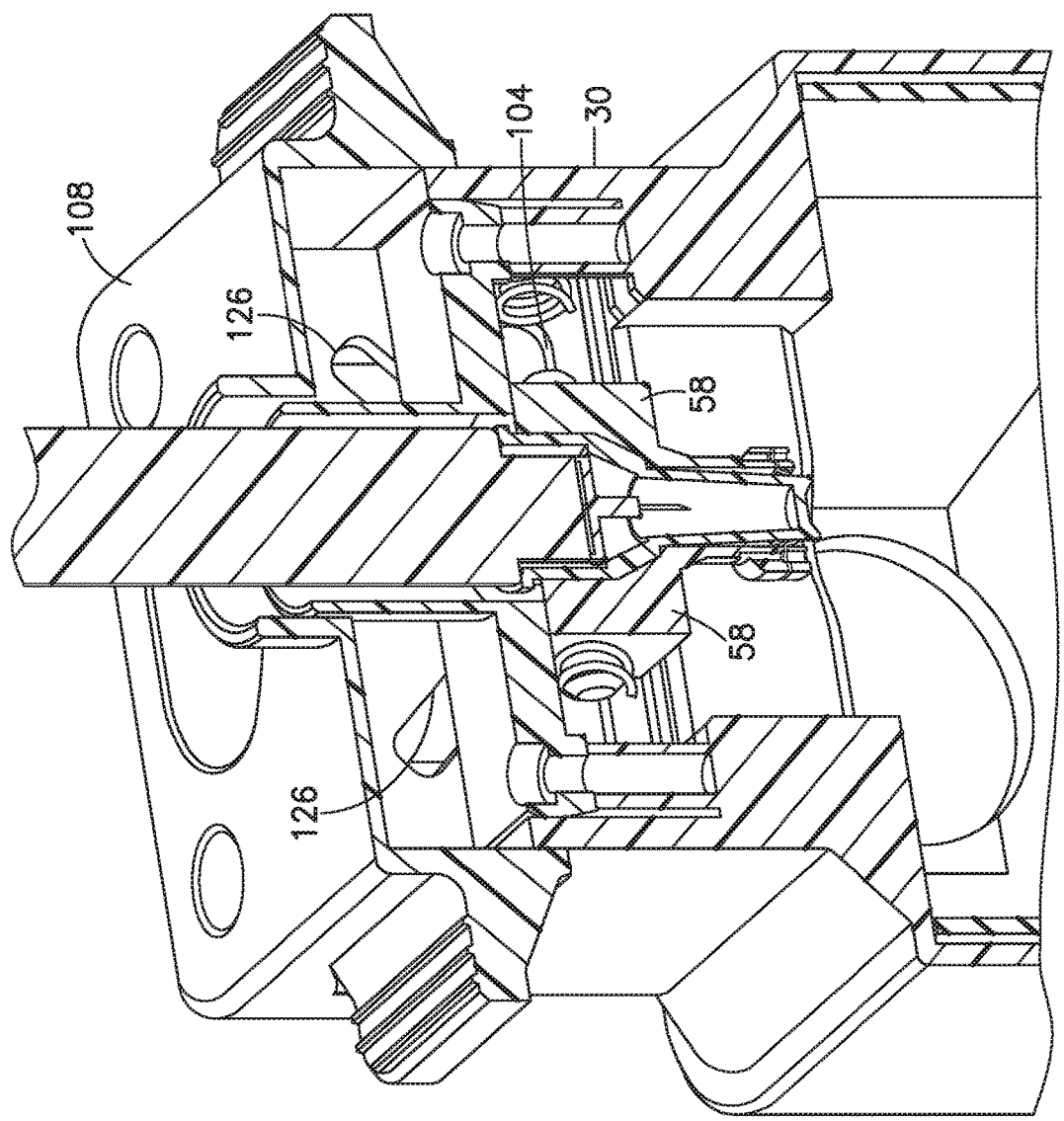
FIG. 21 is a perspective view showing the needle hub returned to the outer cover in the apparatus.
Figure 22:
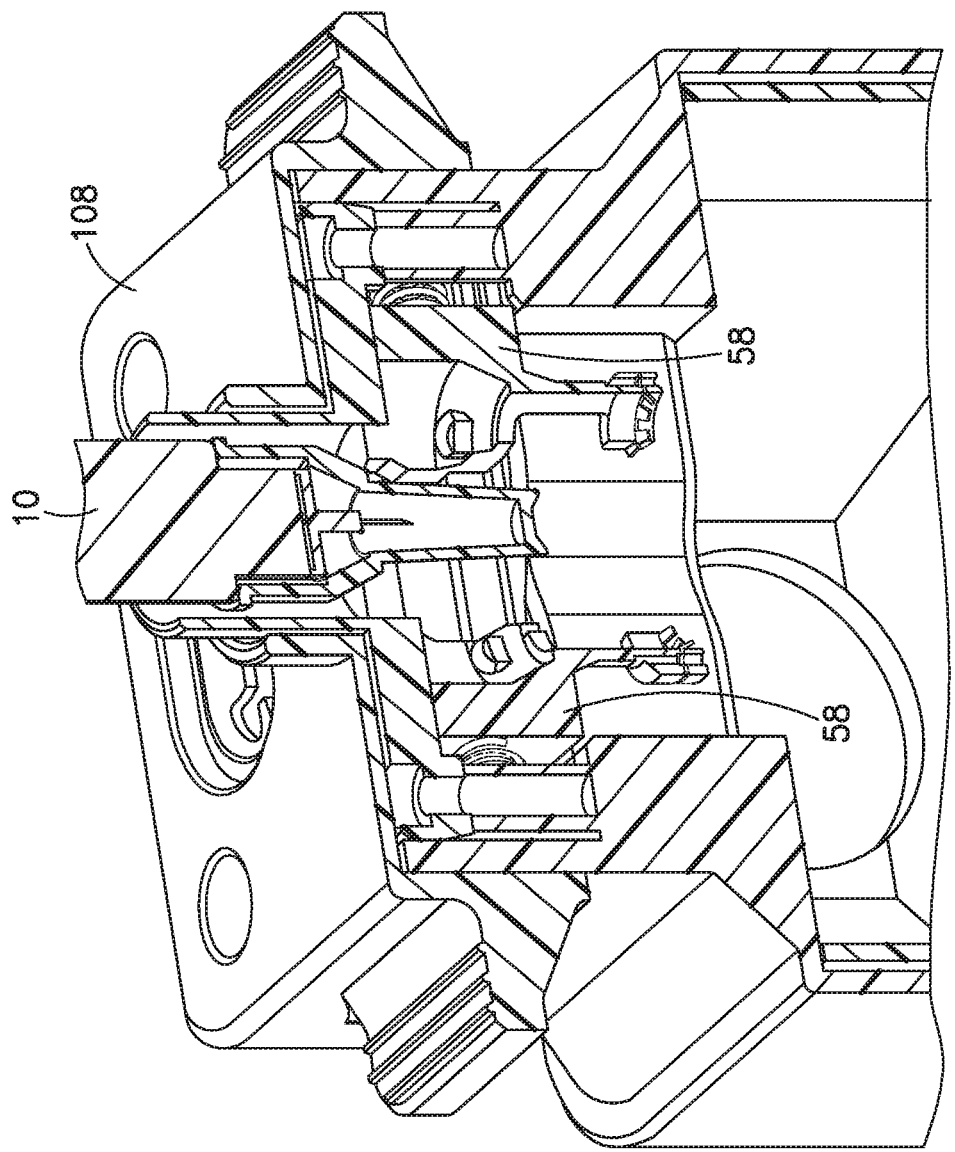
FIG. 22 is a perspective view showing the delivery pen removed with the needle hub and outer cover.

In a further embodiment shown in FIG. 21 and FIG. 22 the outer cover 22 can be re-attached to the hub 16 without separating the needle hub from the delivery pen. The delivery pen with the attached needle hub 16 can be inserted through the collar and the housing so that the needle hub 16 is received in the outer cover 22 as shown in FIG. 21. The actuator 108 can then be depressed to the position shown in FIG. 22 to separate the jaws 58 to release the outer cover 22. The delivery pen can then be withdrawn with the outer cover protecting the cannula to avoid inadvertent needle stick.

In the embodiment of FIGS. 3-22 apparatus is shown with a single opening well for receiving a single pen needle assembly. In alternative embodiments, the assembly can have more than one opening and opposing jaws for accommodating a plurality of pen needle assemblies.

In another embodiment the assembly can include a housing with a plurality of wells for receiving a respective pen needle assembly. An actuator button can be provided for each respective well for operating a gripping mechanism for retaining the outer cover of the pen needle assembly.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives, and variations will be apparent to those of ordinary skill in the art, and are intended to fall within the scope of the invention. It is particularly noted that the features of different embodiments and claims may be combined with each other as long as they do not contradict each other. Accordingly, all such modifications are intended to be included within the scope of this invention as defined in the appended claims and their equivalents.

The invention claimed is:

1. A pen needle assembly apparatus comprising:
 a housing having an inner cavity, a top end, and a bottom end;
 a first jaw and a second jaw configured for gripping an outer cover of a pen needle assembly in a first position and releasing the outer cover in a second position; and
 a movable cover being movable in a linear direction toward the bottom end of the housing, the movable cover including a cam surface engaging the first jaw and the second jaw to move the first jaw and the second jaw from the first position to the second position by movement of the movable cover in the linear direction toward the bottom end of the housing to release the outer cover whereby the outer cover passes into the inner cavity.

2. The pen needle assembly apparatus of claim 1, wherein the housing has an opening configured for receiving and gripping an inner shield of the pen needle assembly.

3. The pen needle assembly apparatus of claim 2, wherein the opening communicates with the inner cavity whereby the inner shield can pass into the inner cavity.

4. The pen needle assembly apparatus of claim 1, wherein the cam surface moves the first jaw and the second jaw in a substantially perpendicular linear direction away from each other to the second position.

5. The pen needle assembly apparatus of claim 4, wherein the first jaw and the second jaw are spring biased toward the first position.

6. The pen needle assembly apparatus of claim 5, wherein the cam surface includes a first cam configured for engaging the first jaw and a second cam surface configured for engaging the second jaw.

7. The pen needle assembly apparatus of claim 6, wherein the movable cover is coupled to the housing for movement in the linear direction from a first extended position where the first jaw and the second jaw are in the first position, and a second depressed position where the first jaw and the second jaw are in the second position.

8. The pen needle assembly apparatus of claim 7, wherein the movable cover is spring biased to the first extended position.

9. A pen needle assembly apparatus for receiving used pen needle assembly, comprising:
 a housing having an inner cavity, a bottom end, a top end, and an opening for engaging an inner shield of a pen needle assembly for removing the inner shield from a hub of the pen needle assembly;
 a first jaw and a second jaw coupled to the housing, the first jaw and the second jaw configured for gripping an outer cover of the pen needle assembly in a first position and being movable to a second position to release the outer cover; and
 a movable cover coupled to the housing being movable in a linear direction toward the bottom end of the housing, the movable cover including a cam surface engaging the first jaw and the second jaw for moving the first jaw and the second jaw from the first position to the second position by movement of the movable cover in the linear direction toward the bottom end of the housing to release the outer cover from the pen needle assembly apparatus.

10. The pen needle assembly apparatus of claim 9, wherein the opening in the housing has an inner dimension to engage the inner shield of the pen needle assembly whereby the hub can be removed from the inner shield.

11. The pen needle assembly apparatus of claim 9, wherein the movable cover is coupled to the housing for movement in the linear direction from a first extended position where the first jaw and the second jaw are in the first position, and a second depressed position where the first jaw and the second jaw are in the second position.

12. The pen needle assembly apparatus of claim 9, wherein the movable cover is coupled to the top end of the housing and movable with respect to the housing from a first extended position to a second depressed position, the movable cover having a first opening aligned with the opening of the housing for received the inner shield, and where the movable cover has a second opening aligned with the first jaw and the second jaw for receiving the pen needle assembly.

13. The pen needle assembly apparatus of claim 9, wherein the movable cover moves in a substantially linear direction perpendicular to a linear direction of movement of the first jaw and the second jaw.

14. The pen needle assembly apparatus of claim 9, wherein the cam surface moves the first jaw and the second jaw in a substantially perpendicular linear direction away from each other to the second position.

15. The pen needle assembly apparatus of claim 14, wherein the cam surface includes a first cam surface engaging the first jaw, and a second cam surface engaging the second jaw, and where movement of the movable cover moves the first jaw and the second jaw away from each other to release the outer cover of the pen needle assembly.

16. The pen needle assembly apparatus of claim 14, wherein the cam surface of the movable cover includes a first slot defining a first cam surface receiving a first cam follower on the first jaw, and a second slot defining a second cam surface receiving a second cam follower on the second jaw.

17. The pen needle assembly apparatus of claim 16, wherein the first slot is oriented at a first inclined angle with respect to a direction of travel of the movable cover, and the second slot is oriented at a second inclined angle with respect to the direction of movement of the movable cover.

18. A method of coupling a pen needle to a delivery pen, the method comprising:
- positioning a pen needle assembly in a pen needle assembly apparatus between a first jaw and a second jaw for gripping an outer cover of the pen needle assembly and attaching the delivery pen to the pen needle assembly;
- removing the delivery pen and a needle hub from the outer cover and inserting an inner shield of the pen needle assembly apparatus into an opening in the pen needle assembly apparatus to grip the inner shield, and removing the inner shield from the needle hub of the pen needle assembly;
- inserting the needle hub after use into the outer cover and separating the delivery pen from the needle hub; and
- depressing a movable cover in a linear direction toward a bottom end of the pen needle assembly apparatus to move the first jaw and the second jaw engaged to a cam surface of the movable cover from (i) a first position to grip the outer cover to (ii) a second position to release the outer cover and the needle hub from the first jaw and the second jaw.

19. The method of claim 18, wherein the cam surface moves the first jaw and the second jaw in a substantially linear direction away from each other to the second position.

20. The method of claim 19, wherein the cam surface includes a first cam surface engaging the first jaw, and a second cam surface engaging the second jaw, and where movement of the movable cover moves the first jaw and the second jaw away from each other to release the outer cover of the pen needle assembly.

* * * * *